(12) United States Patent
Futaki et al.

(10) Patent No.: US 11,179,471 B2
(45) Date of Patent: Nov. 23, 2021

(54) PEPTIDE FOR CYTOSOLIC DELIVERY

(71) Applicant: KYOTO UNIVERSITY, Kyoto (JP)

(72) Inventors: Shiroh Futaki, Kyoto (JP); Kentarou Sakamoto, Kyoto (JP); Misao Akishiba, Kyoto (JP)

(73) Assignee: KYOTO UNIVERSITY, Kyoto (JP)

( * ) Notice: Subject to any disclaimer, the term of this patent is extended or adjusted under 35 U.S.C. 154(b) by 0 days.

(21) Appl. No.: 16/496,405

(22) PCT Filed: Mar. 22, 2018

(86) PCT No.: PCT/JP2018/011406
§ 371 (c)(1),
(2) Date: Sep. 20, 2019

(87) PCT Pub. No.: WO2018/174158
PCT Pub. Date: Sep. 27, 2018

(65) Prior Publication Data
US 2020/0046840 A1    Feb. 13, 2020

(30) Foreign Application Priority Data
Mar. 22, 2017 (JP) .............................. JP2017-055508

(51) Int. Cl.
*A61K 47/42* (2017.01)
*C07K 14/435* (2006.01)
*A61K 9/107* (2006.01)

(52) U.S. Cl.
CPC ............ *A61K 47/42* (2013.01); *A61K 9/1075* (2013.01); *C07K 14/435* (2013.01)

(58) Field of Classification Search
None
See application file for complete search history.

(56) References Cited

U.S. PATENT DOCUMENTS 8,334,366 B1  12/2012  Hughes et al.

FOREIGN PATENT DOCUMENTS

| JP | 2009-007547 A | | 1/2009 |
| WO | WO 2015/038662 A1 | | 3/2015 |
| WO | WO 2016/052442 | * | 4/2016 |
| WO | WO 2016/052442 A1 | | 4/2016 |

OTHER PUBLICATIONS

Burton (Pept Sci, 92: 132-136, 2009) (Year: 2009).*
Futaki et al. (WO 2016/052442, machine translation) (Year: 2016).*
Adão et al., "Membrane structure and interactions of a short Lycotoxin I analogue," *J. Pept. Sci.*, 14(4): 528-534 (2008).
Akishiba et al., "Novel Peptide Sequence for Endosome Disruption Derived from Natural Hemolytic Peptide," *Peptide Science*, 2014: 33-34 (2015).
Akishiba et al., "Cytosolic antibody delivery by lipid-sensitive endosomolytic peptide," *Nat. Chem.*, 9(8): 751-761 (2017).
Akishiba et al., "Introduction of functional protein into cell using endosome-destabilizing peptide," *Annual Abstracts of the Pharmaceutical Society of Japan*, 138: GS02-7 (2018).
Akishiba et al., "Opening entrance to cell: Introduction of Protein into Cell," *Chemistry Today*, 563: 32-36 (2018).
Boussif et al., "A versatile vector for gene and oligonucleotide transfer into cells in culture and in vivo: Polyethylenimine," *Proc. Natl. Acad. Sci. U.S.A.*, 92(16): 7297-7301 (1995).
Hughes et al., "Cell-Penetrating Recombinant Peptides for Potential Use in Agricultural Pest Control Applications," *Pharmaceuticals*, 5(10): 1054-1063 (2012).
Maeda et al., "Interaction of influenza virus hemagglutinin with target membrane lipids is a key step in virus-induced hemolysis and fusion at pH 5.2," *Proc. Natl. Acad. Sci. U.S.A.*, 78(7): 4133-4137 (1981).
Rozema et al., "Endosomolysis by Masking of a Membrane-Active Agent (EMMA) for Cytoplasmic Release of Macromolecules," *Bioconjug. Chem.*, 14(1): 51-57 (2003).
Sakamoto et al., "Design and evaluation of activity improvement in endosome-destabilizing peptide L17E," *Annual Abstracts of the Pharmaceutical Society of Japan*, 137: 25R-pm02S (2017).
Sakamoto et al, "Improvement of activity in endosome destabilizing peptide, and evaluation thereof, paying attention to histidine residue," *Annual Abstracts of the Pharmaceutical Society of Japan*, 138: 26V-pm13S (2018).
Subbarao et al., "pH-Dependent Bilayer Destabilization by an Amphipathic Peptide," *Biochemistry*, 26(11): 2964-2972 (1987).
Takaoka et al., "Protein Organic Chemistry and Applications for Labeling and Engineering in Live-Cell Systems," *Angew. Chem. Int. Ed.*, 52(15): 4088-4106 (2013).
Wadia et al., "Transducible TAT-HA fusogenic peptide enhances escape of TAT-fusion proteins after lipid raft macropinocytosis," *Nat. Med.*, 10(3): 310-315 (2004).
Yan et al., "Detailed folding structures of M-lycotoxin-Hc1a and its mutageneses using 2D HP model," *Molecular Simulation*, 38(10): 809-822 (2012).
Japanese Patent Office, International Search Report in International Patent Application No. PCT/JP2018/011406 (dated Jun. 26, 2018).
Angeles-Boza et al., "Generation of Endosomolytic Reagents by Branching of Cell-Penetrating Peptides: Tools for the Delivery of Bioactive Compounds to Live Cells in Cis or Trans," *Bioconjug. Chem.*, 21(12): 2164-2167 (2010).
Erazo-Oliveras et al., "Improving the Endosomal Escape of Cell-Penetrating Peptides and Their Cargos: Strategies and Challenges," *Pharmaceuticals (Basel)*, 5(11): 1177-1209 (2012).
European Patent Office, Extended European Search Report in European Patent Application No. 1877069.7 (dated Nov. 18, 2020).

* cited by examiner

*Primary Examiner* — Sergio Coffa
(74) *Attorney, Agent, or Firm* — Leydig, Voit & Mayer, Ltd.

(57) ABSTRACT

Provided is a peptide represented by the following formula (I):

$$R^1-IWLTALX^5FLGX^6X^1AAX^7X^2X^3AX^8QX^4LSX^9L-R^2 \quad (I)$$

wherein $X^1$, $X^2$, $X^3$, $X^4$, $X^5$, $X^6$, $X^7$, $X^8$, $X^9$, $R^1$, and $R^2$ are as defined in the specification.

14 Claims, 6 Drawing Sheets
Specification includes a Sequence Listing.

Results are presented as means ± SE (n=3), *; $p<0.05$, ***; $p<0.001$ vs L17E (one-way analysis of variance (ANOVA) followed by Dunnett's multiple comparison post-hoc test)

Fig. 7

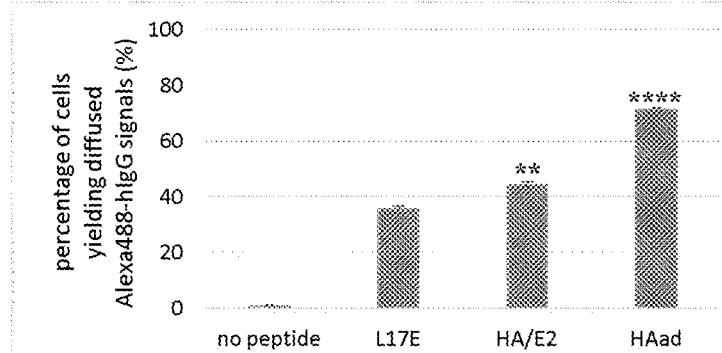

Results are presented as means ± SE (n=3), ; p<0.01, **; p<0.0001 vs L17E (one-way ANOVA followed by Dunnett's multiple comparison post-hoc test)

Fig. 8

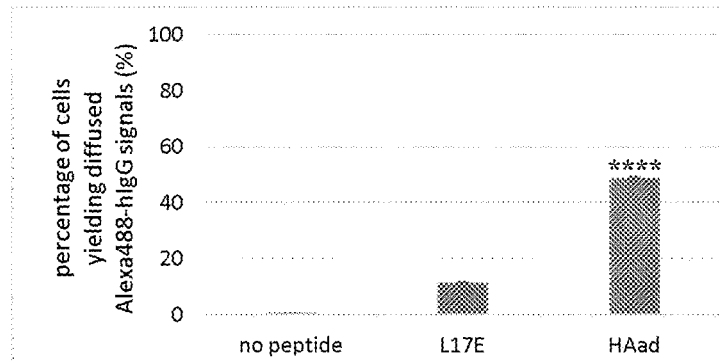

Results are presented as means ± SE (n=3), ****; p<0.0001 vs L17E (one-way ANOVA followed by Dunnett's multiple comparison post-hoc test)

Fig. 9

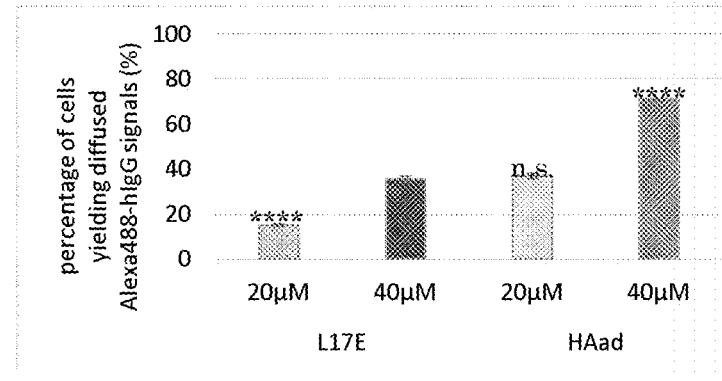

Results are presented as means ± SE (n=3), ****; p<0.0001, n.s.; not significantly different vs 40 µM L17E (one-way ANOVA followed by Dunnett's multiple comparison post-hoc test)

Results are presented as means ± SE (n=3). ****; p<0.0001 vs L17E (one-way ANOVA followed by Dunnett's multiple comparison post-hoc test)

Results are presented as means ± SE (n=3) ***p<0.005 (student's t-test)

Results are presented as means ±SE (n=3). *; p<0.05, ****; p<0.0001, n.s.: not sigunificantly different (One-way ANOVA followed by Dunnett's multiple comparison post-hoc test)

PEPTIDE FOR CYTOSOLIC DELIVERY

CROSS-REFERENCE TO RELATED APPLICATIONS

This patent application is the U.S. national phase of International Patent Application No. PCT/JP2018/011406, filed Mar. 22, 2018, which claims the benefit of Japanese Patent Application No. 2017-055508, filed Mar. 22, 2017, which are incorporated by reference in their entireties herein.

INCORPORATION-BY-REFERENCE OF MATERIAL ELECTRONICALLY SUBMITTED

Incorporated by reference in its entirety herein is a computer-readable nucleotide/amino acid sequence listing submitted concurrently herewith and identified as follows: 4392 bytes ASCII (Text) file named "745927ReplacementSequenceListing.txt," created Sep. 8, 2020.

TECHNICAL FIELD

The present invention relates to a peptide for delivering a target substance to the cytoplasm, a cytoplasmic delivery agent, and a substance-introducing agent.

BACKGROUND ART

The introduction of proteins and nucleic acids into living cells is a very useful approach to measurement and analysis of cell function, and regulation of cell function. For example, the localization and behavior of various intracellular proteins are currently observed by fusion with fluorescent proteins. However, the influence of fusion with fluorescent proteins on the intracellular localization and behavior, and on protein activity, cannot be denied. Further, it is difficult to control the intracellular expression level of fusion proteins. Therefore, in their strict evaluation, examinations are desirably conducted by a plurality of methods. The fluorescent properties of fluorescent proteins to be fused are restricted. If proteins chemically labeled with suitable fluorophores can be introduced into cells, this will help solve these problems. Moreover, various biosensors taking advantage of the recognition ability of natural proteins have recently been developed (NPL 1), and their application to intracellular measurement is expected. However, when such chemically modified proteins are introduced from the outside to the inside of cells, a considerable amount of proteins added from the outside of cells are retained in endosomes, and are not released or diffused into the cytoplasm; thus, the desired function of intracellular visualization and measurement of these proteins cannot be exhibited in many cases.

In recent years, the development of various biopolymeric drugs has rapidly progressed. In particular, antibodies have very high target specificity; thus, their development as molecular-targeted drugs, which can replace low-molecular-weight drugs, has been advanced worldwide. However, because antibodies are generally not transferred into the cytoplasm, the current situation is that their targets are limited to receptors on cell membranes, or extracellular disease-related factors. In the cytoplasm, there are many components that can serve as targets in the treatment of various diseases, such as cytoskeleton-associated proteins and kinase-associated factors. Accordingly, if an efficient method for introducing polymers into cells is established, the scope of application of antibody drugs will be significantly expanded. Further, nucleic acids, such as siRNA (DNA, RNA), and drugs are also target substances of intracellular introduction.

For the above reasons, there is a demand for the establishment of a method for effectively introducing biologically active proteins including antibodies, nucleic acids, and drugs into the cytoplasm of living cells.

Examples of typical endosome-destabilizing peptides, which release proteins and drugs encapsulated in endosomes into the cytoplasm, include GALA (NPL 2), an influenza/hemagglutinin HA2 protein-derived peptide (NPL 3), and the like. These are pH-dependent membrane fusion peptides. When the endosomal pH is about 5, these peptides are considered to exhibit membrane fusion properties, disrupt the endosomal membrane, and release encapsulated substances into the cytoplasm. Further, there is a report of a linked product of HIV-1 Tat peptide, which is known as a membrane-permeable peptide, and HA2 peptide (NPL 4) etc., and there is a report of an example using it for intracellular introduction of biologically active proteins, such as a fusion protein of Cre and Tat.

Moreover, there is a report of an attempt to, in bee venom melittin having high membrane-damaging properties, protect the basic amino acid lysine with a pH-sensitive maleic acid derivative, and allow the protecting group to be removed due to pH decrease in endosomes, thereby selectively disrupting the endosomal membrane, so that endosome-encapsulated substances are released into the cytoplasm (NPL 5).

Furthermore, it is reported that because the degree of protonation of polycationic polymers, such as polyethyleneimine, increases in accordance with pH decrease, swelling of the endosome is induced, and the contents (e.g., nucleic acid) are released into the cytoplasm (proton sponge effect: NPL 6). In addition, various pH-responsive polymers are used for gene transfer (PTL 1).

PTL 2 discloses a peptide that can introduce proteins, including antibodies, into living cells. However, there was room for improvement in its introduction efficiency.

CITATION LIST

Patent Literature

PTL 1: JP2009-007547A
PTL 2: WO2016/052442

Non-Patent Literature

NPL 1: Takaoka et al., Angew. Chem. Int. Ed. 2013, 52, 4088
NPL 2: Subbarao et al., Biochemistry 1987, 26, 2964
NPL 3: Maeda et al., PNAS 1981, 78, 4133
NPL 4: Wadia et al., Nature Med. 2004, 10, 310
NPL 5: Rozema et al., Bioconjug. Chem., 2003, 14, 51
NPL 6: Boussif et al., PNAS 1995, 92, 7297

SUMMARY OF INVENTION

Technical Problem

For effective cell function measurement and analysis, it is desirable that most of extracellularly introduced biologically active proteins, nucleic acids, drugs, fluorescently labeled proteins, and sensor molecules can be introduced into the cytoplasm, in which function and activity are developed. However, conventional methods had problems in that these molecules incorporated by endocytosis, which is the physiological uptake mechanism of cells, could not be released, with satisfactory efficiency, from endosomes to the cytoplasm. In terms of delivery of biopharmaceuticals into cells, it is expected to effectively deliver proteins (e.g., antibodies), nucleic acids, and drugs incorporated by endocytosis to the cytoplasm. However, there has been no report of any method that can release, with satisfactory efficiency, proteins (e.g., antibodies), nucleic acids, and drugs into the cytoplasm.

An object of the present invention is to efficiently deliver, to the cytoplasm, target substances, such as proteins, nucleic acids, and drugs, incorporated by endocytosis.

Solution to Problem

The present inventors found that the release of target substances, such as antibodies, sensor molecules, nucleic acids, and drugs, from endosomes to the cytoplasm could be accelerated by substituting some of the amino acids of basic amphiphilic peptide lycotoxin with acidic amino acids.

The present invention provides a cytoplasmic delivery agent for target substances, such as peptides, proteins, nucleic acids, and drugs, and also relates to a substance-introducing agent, described below.

Item 1. A peptide represented by the following formula (I):

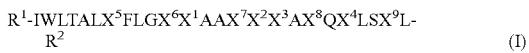

$$R^1\text{-IWLTALX}^5\text{FLGX}^6X^1\text{AAX}^7X^2X^3\text{AX}^8\text{QX}^4\text{LSX}^9\text{L-}R^2 \quad \text{(I)}$$

wherein $X^1$ and $X^2$ are the same or different, and each represents H or A;

$X^3$ represents E, L-2-aminoadipic acid (Aad), 2-aminopimelic acid, or 2-aminosuberic acid;

$X^4$ represents Q, L-2-aminoadipic acid (Aad), 2-aminopimelic acid, 2-aminosuberic acid, or E;

$X^5$ to $X^9$ are the same or different, and each represents Lys (K), Arg (R), homoarginine, ornithine, homolysine, or 2-amino-7-guanidinoheptanoic acid;

provided that a case where $X^1$=H, $X^2$=H, $X^3$=E, $X^4$=Q, and $X^5$ to $X^9$=K is excluded, and when $X^4$=E, and $X^5$ to $X^9$=K, one or both of $X^1$ and $X^2$ are A;

$R^1$ represents a hydrogen atom, an alkyl group, an acyl group, an alkoxycarbonyl group, an aralkyloxycarbonyl group, an aryloxycarbonyl group, or a target substance; and $R^2$ represents a hydroxyl group (OH), an amino group ($NH_2$), a monoalkylamino group, a monoarylamino group, monocycloalkylamino, a dialkylamino group, an alkoxy group, an aralkyloxy group, an aryloxy group, or a target substance.

Item 2. The peptide according to Item 1 represented by any one of the following formulas (Ia) to (Ie):

$$R^1\text{-IWLTALX}^5\text{FLGX}^6\text{AAAX}^7\text{AEAX}^8\text{QELSX}^9\text{L-}R^2 \quad \text{(Ia)},$$

$$R^1\text{-IWLTALX}^5\text{FLGX}^6\text{HAAX}^7\text{HXAX}^8\text{QQLSX}^9\text{L-}R^2 \quad \text{(Ib)},$$

$$R^1\text{-IWLTALX}^5\text{FLGX}^6\text{AAAX}^7\text{AXAX}^8\text{QXLSX}^9\text{L-}R^2 \quad \text{(Ic)},$$

$$R^1\text{-IWLTALX}^5\text{FLGX}^6\text{AAAX}^7\text{AEAX}^8\text{QQLSX}^9\text{L-}R^2 \quad \text{(Id), and}$$

$$R^1\text{-IWLTALX}^5\text{FLGX}^6\text{HAAX}^7\text{HXAX}^8\text{QXLSX}^9\text{L-}R^2 \quad \text{(Ie)};$$

wherein X represents L-2-aminoadipic acid (Aad), 2-aminopimelic acid, or 2-aminosuberic acid;

$R^1$=represents a hydrogen atom, an alkyl group, an acyl group, an alkoxycarbonyl group, an aralkyloxycarbonyl group, an aryloxycarbonyl group, or a target substance;

$R^2$ represents a hydroxyl group (OH), an amino group ($NH_2$), a monoalkylamino group, a monoarylamino group, monocycloalkylamino, a dialkylamino group, an alkoxy group, an aralkyloxy group, an aryloxy group, or a target substance; and $X^5$ to $X^9$ are the same or different, and each represents Lys (K), Arg (R), homoarginine, ornithine, homolysine, or 2-amino-7-guanidinoheptanoic acid.

Item 3. The peptide according to Item 2 represented by any one of the following formulas (Ia) to (Ic):

$$R^1\text{-IWLTALX}^5\text{FLGX}^6\text{AAAX}^7\text{AEAX}^8\text{QELSX}^9\text{L-}R^2 \quad \text{(Ia)},$$

$$R^1\text{-IWLTALX}^5\text{FLGX}^6\text{HAAX}^7\text{HXAX}^8\text{QQLSX}^9\text{L-}R^2 \quad \text{(Ib), and}$$

$$R^1\text{-IWLTALX}^5\text{FLGX}^6\text{AAAX}^7\text{AXAX}^8\text{QXLSX}^9\text{L-}R^2 \quad \text{(Ic)};$$

wherein X represents L-2-aminoadipic acid (Aad), 2-aminopimelic acid, or 2-aminosuberic acid;

$R^1$ represents a hydrogen atom, an alkyl group, an acyl group, an alkoxycarbonyl group, an aralkyloxycarbonyl group, an aryloxycarbonyl group, or a target substance;

$R^2$ represents a hydroxyl group (OH), an amino group ($NH_2$), a monoalkylamino group, a monoarylamino group, monocycloalkylamino, a dialkylamino group, an alkoxy group, an aralkyloxy group, an aryloxy group, or a target substance; and $X^5$ to $X^9$ are the same or different, and each represents Lys (K), Arg (R), homoarginine, ornithine, homolysine, or 2-amino-7-guanidinoheptanoic acid.

Item 4. A cytoplasmic delivery agent comprising the peptide according to any one of Items 1 to 3.

Item 5. A cytoplasm-targeted substance-introducing agent comprising the peptide according to any one of Items 1 to 3 in a vector.

Item 6. A cytoplasm-targeted substance-introducing agent comprising the peptide according to any one of items 1 to 3; and a target substance covalently bonded directly or via a spacer to the peptide.

Item 7. A cytoplasm-targeted substance-introducing agent comprising a composite having the peptide according to any one of items 1 to 3; and a target substance non-covalently bonded directly or via a molecule to the peptide, the molecule interacting with the target substance.

Item 8. The cytoplasm-targeted substance-introducing agent according to Item 5, wherein a target substance is encapsulated in the vector.

Item 9. The substance-introducing agent according to Item 5, wherein the peptide is bonded to a constituent of the vector directly or via a spacer.

Item 10. The substance-introducing agent according to Item 4, 5, 6, or 7, comprising a conjugate of the peptide and a molecule that increases the affinity of the peptide to a target cell.

Item 11. The substance-introducing agent according to Item 5, 8, or 9, wherein the peptide is encapsulated in the vector, together with a target substance.

Item 12. The substance-introducing agent according to Item 5, 8, or 9, wherein the vector is a liposome, a lipid microsphere, a polymer micelle, a polymer hollow carrier, a nanogel, a high-density lipoprotein (HDL), a synthetic polymer, a self-assembled nucleic acid-derived vector, a virus outer shell protein-derived vector, or a nanoparticle.

Item 13. The substance-introducing agent according to Item 9, wherein the constituent of the vector is cholesterol or a phospholipid, and the vector comprises a composite comprising cholesterol or a phospholipid, and the peptide according to any one of Items 1 to 3.

Item 14. A peptide represented by the following formula (IA):

$$R^1\text{-}(IWLTALX^5FLGX^6X^1AAX^7X^2X^3AX^8QX^4LSX^9L\text{-}Y)_n\text{-}R^2 \quad (IA)$$

wherein $X^1$ and $X^2$ are the same or different, and each represents H or A;

$X^3$ represents E, L-2-aminoadipic acid (Aad), 2-aminopimelic acid, or 2-aminosuberic acid;

$X^4$ represents Q, L-2-aminoadipic acid (Aad), 2-aminopimelic acid, 2-aminosuberic acid, or E;

$X^5$ to $X^9$ are the same or different, and each represents Lys (K), Arg (R), homoarginine, ornithine, homolysine, or 2-amino-7-guanidinoheptanoic acid;

provided that a case where $X^1$=H, $X^2$=H, $X^3$=E, $X^4$=Q, and $X^5$ to $X^9$=K is excluded, and when $X^4$=E, and $X^5$ to $X^9$=K, one or both of $X^1$ and $X^2$ are A;

$R^1$ represents a hydrogen atom, an alkyl group, an acyl group, an alkoxycarbonyl group, an aralkyloxycarbonyl group, an aryloxycarbonyl group, an alkoxy group, an aralkyloxy group, an aryloxy group, or a target substance;

$R^2$ represents a hydroxyl group (OH), an amino group ($NH_2$), a monoalkylamino group, a monoarylamino group, monocycloalkylamino, a dialkylamino group, an alkoxy group, an aralkyloxy group, an aryloxy group, or a target substance;

Y represents a single bond or a spacer; and n is 2, 3, 4, 5, 6, 7, 8, 9 or 10.

Item 15. A formula (IB) shown below:

$$Z\text{—}(R^a)_m \quad (IB)$$

wherein Z represents a branched multivalent linker;

$R^a$ is the same or different, and each represents $R^1\text{-}IWLTALX^5FLGX^6X^1AAX^7X^2X^3AX^8QX^4LSX^9L\text{-}Y\text{-}$ or $Y\text{-}IWLTALX^5FLGX^6X^1AAX^7X^2X^3AX^8QX^4LSX^9L\text{-}R^2$;

wherein $X^1$ and $X^2$ are the same or different, and each represents H or A;

$X^3$ represents E, L-2-aminoadipic acid (Aad), 2-aminopimelic acid, or 2-aminosuberic acid;

$X^4$ represents Q, L-2-aminoadipic acid (Aad), 2-aminopimelic acid, 2-aminosuberic acid, or E;

$X^5$ to $X^9$ are the same or different, and each represents Lys (K), Arg (R), homoarginine, ornithine, homolysine, or 2-amino-7-guanidinoheptanoic acid;

provided that a case where $X^1$=H, $X^2$=H, $X^3$=E, $X^4$=Q, and $X^5$ to $X^9$=K is excluded, and when $X^4$=E, and $X^5$ to $X^9$=K, one or both of $X^1$ and $X^2$ are A;

$R^1$ represents a hydrogen atom, an alkyl group, an acyl group, an alkoxycarbonyl group, an aralkyloxycarbonyl group, an aryloxycarbonyl group, an alkoxy group, an aralkyloxy group, an aryloxy group, or a target substance;

$R^2$ represents a hydroxyl group (OH), an amino group ($NH_2$), a monoalkylamino group, a monoarylamino group, monocycloalkylamino, a dialkylamino group, an alkoxy group, an aralkyloxy group, an aryloxy group, or a target substance;

Y represents a single bond or a spacer; and m is an integer of 2 to 8.

Advantageous Effects of Invention

The peptide of the present invention has such an effect that it effectively interacts with cell surfaces to be thereby incorporated into endosomes, together with target substances (intracellularly introduced molecules) such as proteins (e.g., antibodies), nucleic acids, and drugs.

The peptide of the present invention has an effect of inducing destabilization of the endosomal membrane in accordance with pH decrease in the endosome, and changes in the membrane constituents associated with endosomal maturation; and promoting the release of target substances, such as antibodies, sensor molecules, nucleic acids, and drugs, transferred into the endosome together with the peptide, into the cytoplasm.

The peptide of the present invention has an effect of allowing, through delivery of chemically modified (e.g., fluorescently labeled) target substances, such as proteins and sensor molecules, into the cytoplasm, the measurement and control of the intracellular localization and behavior of the target substances, and the intracellular environment.

The peptide of the present invention has an effect of delivering large physiologically active substances, such as antibodies and nucleic acids, into the cytoplasm.

A first preferable embodiment of the present invention is alanine substitution of histidine residues at positions 12 and 16.

L17E of PTL 2 contains two histidines (H). Histidine is considered to be uncharged at an extracellular pH, and positively charged at the endosomal pH. The endosomal membrane-selective damage of L17E was considered to be enhanced by the positive charge of histidine; however, it was unexpectedly found that the damage was reduced due to the histidine residues. Therefore, an attempt was made to enhance the endosomal membrane-selective damage by substituting the histidine residues at positions 12 and 16 with alanine.

HA/E1 in which two histidine residues were substituted with alanine showed a higher helicity than L17E (FIG. 1), and the activity to release Alexa 488-dextran from endosomes as a macromolecular drug model was largely increased (FIG. 2).

Further, H12A/H16A/L17E/Q21E substitution product (=HA/E2) in which the residue at position 21 was substituted with Glu (E) showed high helicity in the presence of an acidic lipid membrane (FIG. 1), and had endosome-encapsulated substance releasing activity equivalent to that of HA/E1 (FIG. 2). Moreover, the substitution product had significantly higher endosome-encapsulated substance releasing activity than L17E.

The activity of H12Q/H16Q/L17E/Q21E and H12S/H16S/L17E/Q21E, in which the histidines at positions 12 and 16 were substituted with hydrophilic amino acids (glutamine, serine) other than alanine, was inferior to that of L17E. It was concluded that alanine was desirable for substitution of histidine.

A second preferable embodiment of the present invention is substitution of the residues at positions 17 (E) and 21 (Q) with 2-aminoadipic acid (Aad), 2-aminopimelic acid, or 2-aminosuberic acid.

In expectation of further stabilization of the peptide helical structure and enhancement of membrane affinity, a derivative (L17Aad) was synthesized by substituting the glutamic acid (E) at position 17 of L17E, which plays an important role in the selective destabilization of endosomal membranes for cell membranes, with 2-aminoadipic acid (Aad) having one additional methylene chain as a side chain. Due to the presence of histidine residue in the sequence, the helicity of L17Aad itself was not increased so much (FIG. 1); however, as shown in FIG. 3, it was clarified that the endosome-encapsulated substance releasing activity was significantly higher than L17E.

A third preferable embodiment of the present invention is alanine substitution of the histidine residues at positions 12 and 16, and further substitution of the glutamic acid residue at position 17 with 2-aminoadipic acid (Aad), 2-aminopimelic acid, or 2-aminosuberic acid.

Based on the results obtained in the first and second preferable embodiments, peptide HAad was synthesized by substituting the histidine of L17E with alanine, and substituting the glutamic acid at position 17 with aminoadipic acid. As shown in FIG. 1, it was clarified that HAad had high helicity in the presence of an acidic lipid membrane. As shown in FIG. 4 and the Examples, it was clarified that HAad had activity to much more effectively release the drug incorporated in endosomes into the cytoplasm, compared with L17E.

A fourth preferable embodiment of the present invention is substitution of the five Lys (K) residues with Arg (R), homoarginine, ornithine, homolysine, or 2-amino-7-guanidinoheptanoic acid.

Helicity (%)=−($[\theta]_{222}$+2340)/30300*100.

Figure 2:
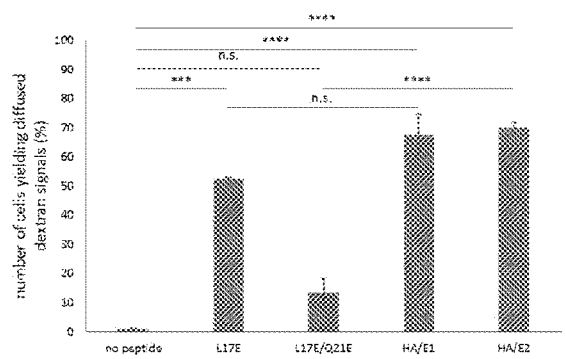

FIG. 2 shows the cell (%) in which the model macromolecular drug Alexa 488-dextran (10 kDa) was observed to be released into the cytoplasm. Cells; HeLa, peptides; 40 µM, Alexa 488-dextran (10 kDa); 200 µg/mL, treatment; 1 hr in α-MEM(−). Results are presented as means ±SE (n=3). *; $p<0.001$, **; $p<0.0001$, n.s.; not significantly different (one-way ANOVA followed by the Tukey-Kramer honestly significant difference test (post-hoc test)).

Figure 3:
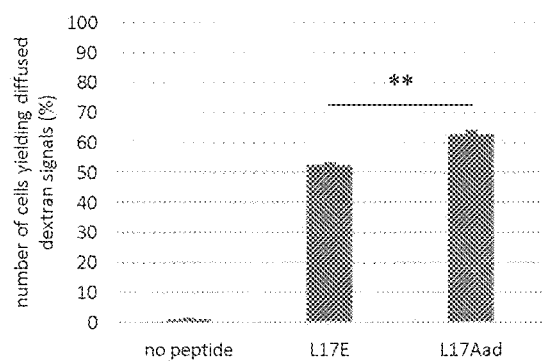

FIG. 3 shows the cell (%) in which the model macromolecular drug Alexa 488-dextran (10 kDa) was observed to be released into the cytoplasm. Cells; HeLa, peptides; 40 µM, Alexa 488-dextran (10 kDa); 200 µg/mL, treatment; 1 hr in α-MEM(−). The results are presented as means ±SE (n=3). **; $p<0.01$ (Student's t-test).

Figure 4:
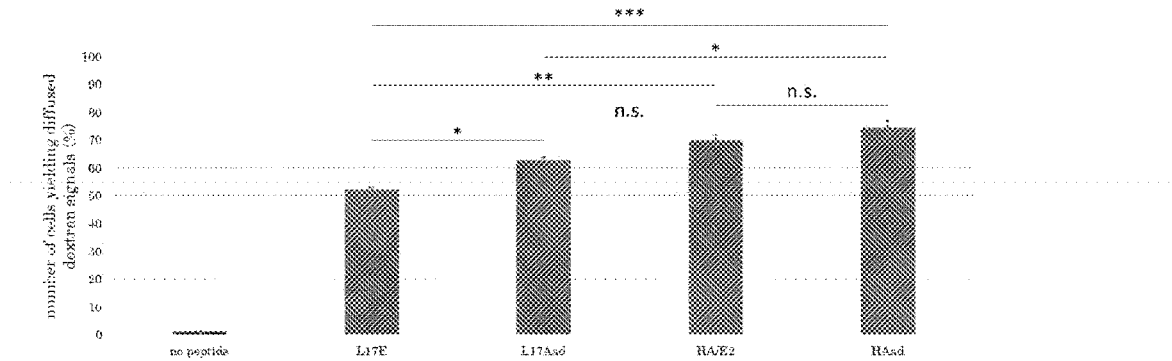

FIG. 4 shows the cell (%) in which the model polymer drug Alexa 488-dextran (10 kDa) was observed to be released into the cytoplasm. HAad, HA/E2, and L17Aad had a higher endosomal content release activity than L17E. Cells; HeLa, peptides; 40 µM, Alexa 488-dextran (10 kDa); 200 µg/mL, treatment; 1 hr in α-MEM(−). Results are presented as means±SE (n=3). *; $p<0.05$, ; $p<0.01$, *; $p<0.001$ (one-way ANOVA followed by the Tukey-Kramer honestly significant difference test (post-hoc test)).

Figure 5:
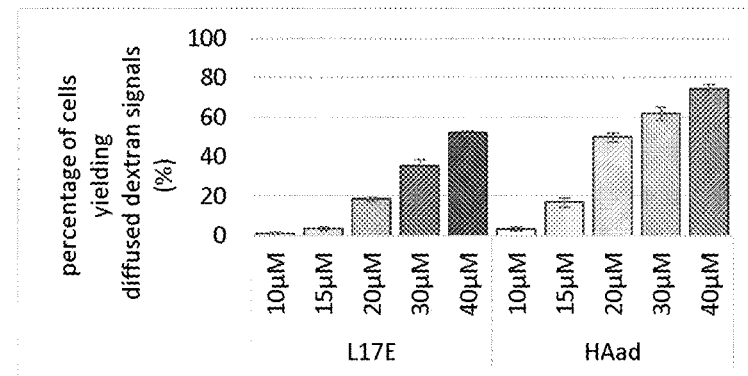

FIG. 5 shows a comparison (1) of efficiency of intracellular release of dextran (10 kDa).

Figure 6:
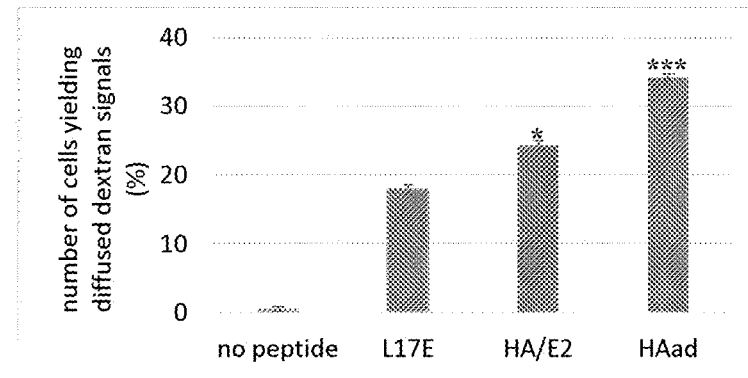

FIG. 6 shows a comparison (2) of efficiency of intracellular release of dextran (10 kDa).

FIG. 7 shows a comparison (1) of efficiency of intracellular release of human immunoglobulin (IgG, circa 160 kDa).

FIG. 8 shows a comparison (2) of efficiency of intracellular release of human immunoglobulin (IgG, circa 160 kDa).

FIG. 9 shows a comparison (3) of efficiency of intracellular release of human immunoglobulin (IgG, circa 160 kDa).

Figure 10:
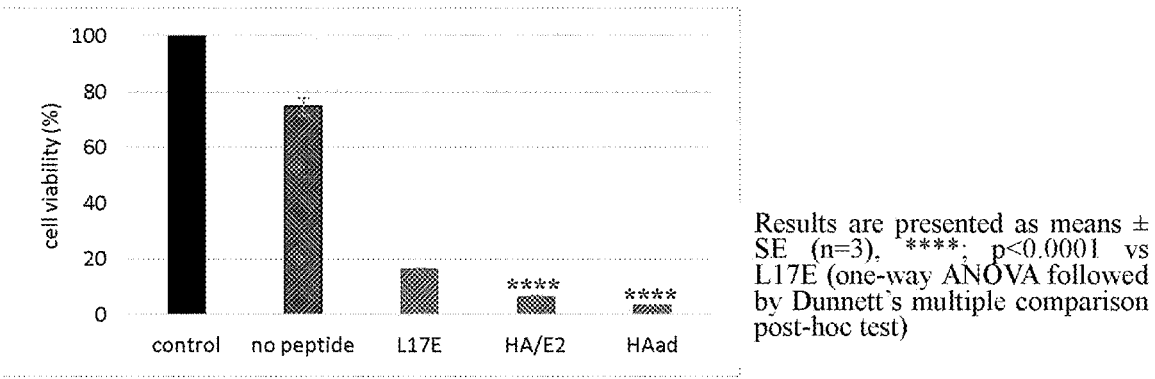

FIG. 10 shows the results of a cell-killing assay by intracellular delivery of toxin protein saporin.

Figure 11:
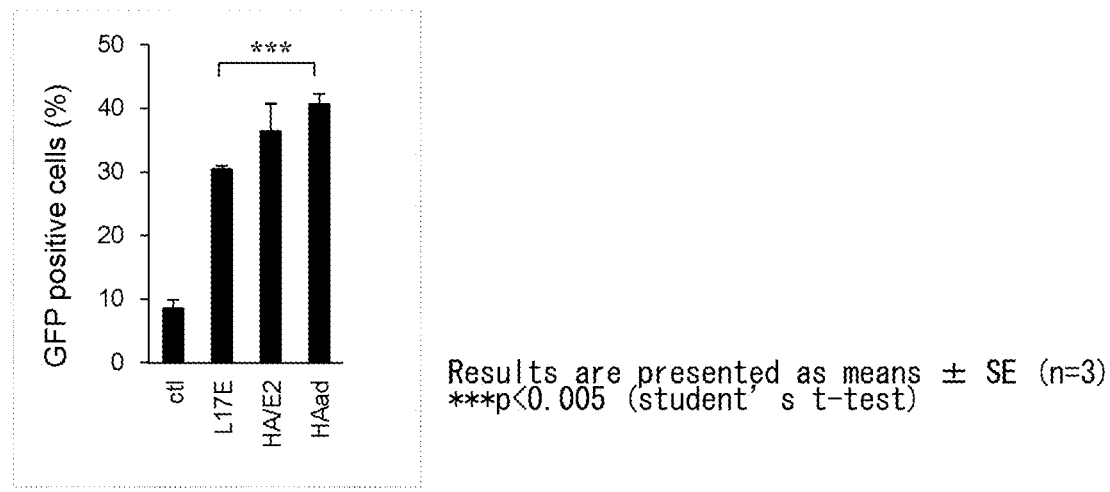

FIG. 11 shows the results of a genetic recombination assay by intracellular delivery of Cre protein.

Figure 12:
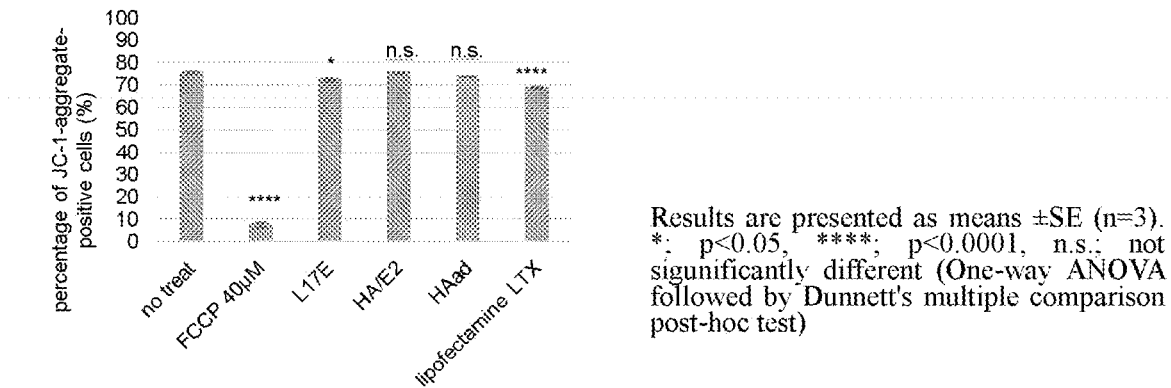

FIG. 12 shows mitochondrial damage by peptide treatment.

Figure 13:
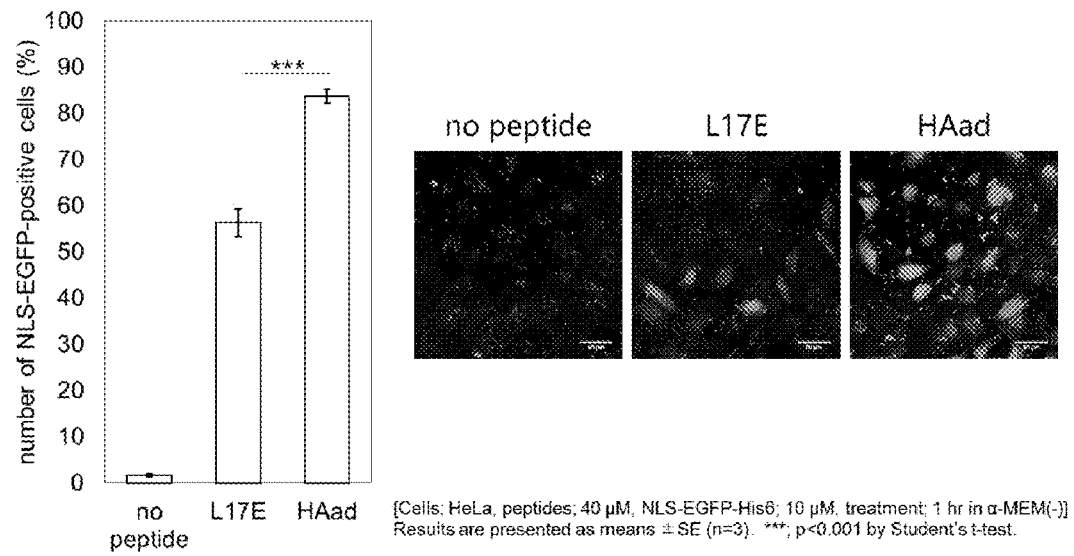

FIG. 13 shows nuclear accumulation of NLS-EGFP. A fusion protein of nuclear localization signal (NLS) and enhanced green fluorescent protein (EGFP) (the internalization was confirmed by nuclear accumulation of the protein that enters cells): a high activity of HAad to release endosome-encapsulated substances was also confirmed in this system.

Figure 14:
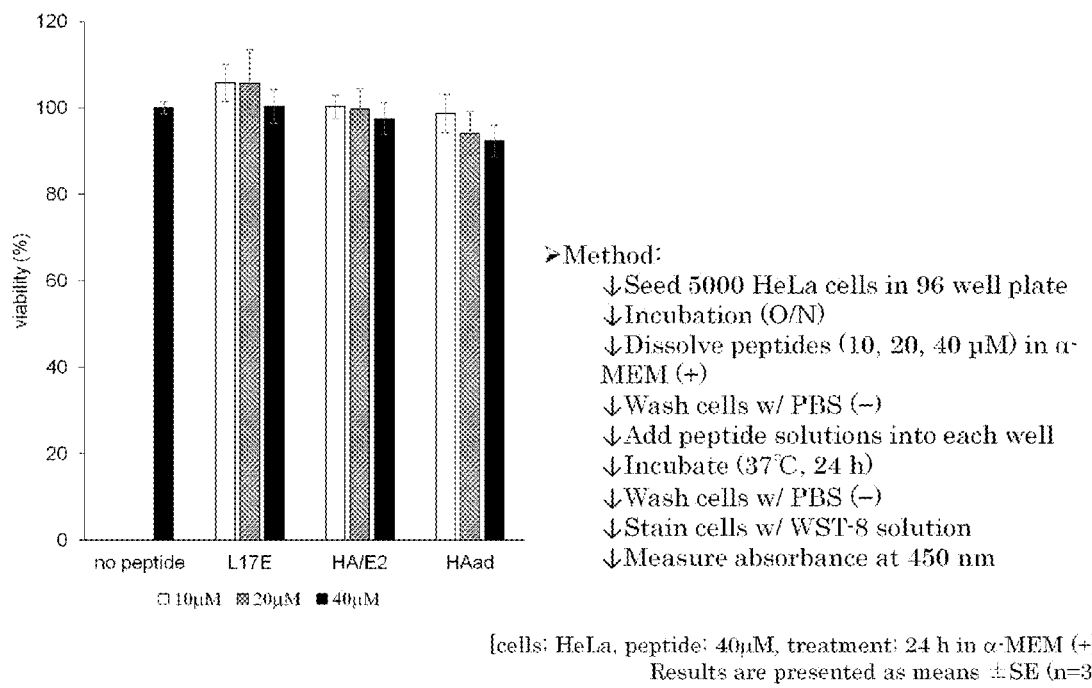

FIG. 14 shows the evaluation of cell viability (%) 24 hours after peptide treatment in the presence of serum.

Figure 15:
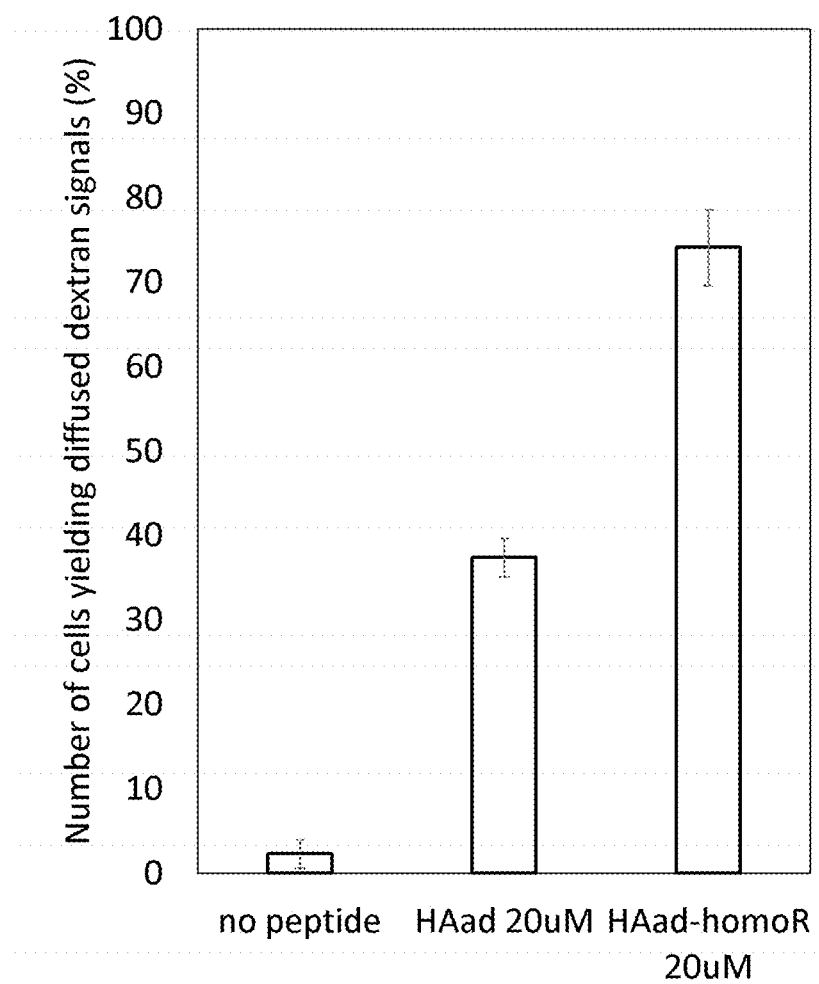

FIG. 15 shows the activity of peptides obtained in Example 16 to release Alexa 488-dextran (10 kDa) into the cytoplasm.

DESCRIPTION OF EMBODIMENTS

The peptide of the present invention is a derivative of the following L17E described in PTL 2:
L17E:

(SEQ ID NO: 1)
IWLTALX$^5$FLGX$^6$HAAX$^7$HEAX$^8$QQLSX$^9$L-amide wherein $X^5$ to $X^9$ are Lys (K).

Specifically, the peptide of the present invention is a peptide in which at least one of H (His) at position 12 corresponding to $X^1$, H (His) at position 16 corresponding to $X^2$, E (Glu) at position 17 corresponding to $X^3$, and Q (Gln) at position 21 corresponding to $X^4$ of Lycotoxin 1 is substituted. H (His) at positions 12 and 16 may be substituted with A (Ala), and E (Glu) at position 17 and Q (Gln) at position 21 may be substituted with X (L-2-aminoadipic acid, Aad, 2-aminopimelic acid, or 2-aminosuberic acid). Moreover, the five Lys (K) residues may be substituted with Arg (R), homoarginine, ornithine, homolysine, or a 2-amino-7-guanidinoheptanoic acid residue.

The peptides of the general formula (I) of the present invention include the following 17 peptides (I-1) to (I-17):

| | |
|---|---|
| R$^1$-IWLTALX$^5$FLGX$^6$X$^1$AAX$^7$X$^2$X$^3$AX$^8$QXLSX$^9$L-R$^2$ | (I) |
| R$^1$-IWLTALX$^5$FLGX$^6$AAAX$^7$HEAX$^8$QQLSX$^9$L-R$^2$ | (I-1) |
| R$^1$-IWLTALX$^5$FLGX$^6$HAAX$^7$AEAX$^8$QQLSX$^9$L-R$^2$ | (I-2) |
| R$^1$-IWLTALX$^5$FLGX$^6$HAAX$^7$HXAX$^8$QQLSX$^9$L-R$^2$ | (I-3) |
| R$^1$-IWLTALX$^5$FLGX$^6$HAAX$^7$HEAX$^8$QXLSX$^9$L-R$^2$ | (I-4) |
| R$^1$-IWLTALX$^5$FLGX$^6$AAAX$^7$AEAX$^8$QQLSX$^9$L-R$^2$ | (I-5) |
| R$^1$-IWLTALX$^5$FLGX$^6$AAAX$^7$AEAX$^8$QELSX$^9$L-R$^2$ | (I-6) |
| R$^1$-IWLTALX$^5$FLGX$^6$AAAX$^7$HXAX$^8$QQLSX$^9$L-R$^2$ | (I-7) |
| R$^1$-IWLTALX$^5$FLGX$^6$AAAX$^7$HEAX$^8$QXLSX$^9$L-R$^2$ | (I-8) |
| R$^1$-IWLTALX$^5$FLGX$^6$HAAX$^7$AXAX$^8$QQLSX$^9$L-R$^2$ | (I-9) |
| R$^1$-IWLTALX$^5$FLGX$^6$HAAX$^7$AEAX$^8$QXLSX$^9$L-R$^2$ | (I-10) |
| R$^1$-IWLTALX$^5$FLGX$^6$HAAX$^7$HXAX$^8$QXLSX$^9$L-R$^2$ | (I-11) |
| R$^1$-IWLTALX$^5$FLGX$^6$AAAX$^7$AXAX$^8$QQLSX$^9$L-R$^2$ | (I-12) |
| R$^1$-IWLTALX$^5$FLGX$^6$AAAX$^7$AXAX$^8$QELSX$^9$L-R$^2$ | (I-13) |

$R^1$-IWLTALX$^5$FLGX$^6$AAAX$^7$AEAX$^8$QXLSX$^9$L-$R^2$     (I-14)

$R^1$-IWLTALX$^5$FLGX$^6$AAAX$^7$HXAX$^8$QXLSX$^9$L-$R^2$     (I-15)

$R^1$-IWLTALX$^5$FLGX$^6$HAAX$^7$AXAX$^8$QXLSX$^9$L-$R^2$     (I-16)

$R^1$-IWLTALX$^5$FLGX$^6$AAAX$^7$AXAX$^8$QXLSX$^9$L-$R^2$     (I-17)

wherein X, $X^1$, $X^2$, $X^3$, $X^4$, $X^5$, $X^6$, $X^7$, $X^8$, $X^9$, $R^1$, and $R^2$ are as defined above.

Preferable peptides of the present invention are the following 5 peptides:

$R^1$-IWLTALX$^5$FLGX$^6$AAAX$^7$AEAX$^8$QELSX$^9$L-$R^2$     (I-6)

$R^1$-IWLTALX$^5$FLGX$^6$HAAX$^7$HXAX$^8$QQLSX$^9$L-$R^2$     (I-3)

$R^1$-IWLTALX$^5$FLGX$^6$AAAX$^7$AXAX$^8$QXLSX$^9$L-$R^2$     (I-17)

$R^1$-IWLTALX$^5$FLGX$^6$AAAX$^7$AEAX$^8$QQLSX$^9$L-$R^2$     (I-5)

$R^1$-IWLTALX$^5$FLGX$^6$HAAX$^7$HXAX$^8$QXLSX$^9$L-$R^2$     (I-11)

wherein X, $R^1$, $R^2$, $X^5$, $X^6$, $X^7$, $X^8$, and $X^9$ are as defined above.

More preferable peptides of the present invention are the following 3 peptides:

$R^1$-IWLTALX$^5$FLGX$^6$AAAX$^7$AEAX$^8$QELSX$^9$L-$R^2$     (I-6)

$R^1$-IWLTALX$^5$FLGX$^6$HAAX$^7$HXAX$^8$QQLSX$^9$L-$R^2$     (I-3)

$R^1$-IWLTALX$^5$FLGX$^6$AAAX$^7$AXAX$^8$QXLSX$^9$L-$R^2$     (I-17)

wherein X, $R^1$, $R^2$, $X^5$, $X^6$, $X^7$, $X^8$, and $X^9$ are as defined above.

Particularly preferable peptides of the present invention are shown below.
HA/E2: IWLTALX$^5$FLGX$^6$AAAX$^7$AEAX$^8$QELSX$^9$L-amide
L17Aad: IWLTALX$^5$FLGX$^6$HAAX$^7$HXAX$^8$QQLSX$^9$L-amide
HAad: IWLTALX$^5$FLGX$^6$AAAX$^7$AXAX$^8$QXLSX$^9$L-amide
HA/E1: IWLTALX$^5$FLGX$^6$AAAX$^7$AEAX$^8$QQLSX$^9$L-amide
L17Aad/Q21Aad:
IWLTALX$^5$FLGX$^6$HAAX$^7$HXAX$^8$QXLSX$^9$L-amide
(X=L-2-aminoadipic acid (Aad), $X^5$ to $X^9$=Lys (K))
HAad-homoR:
IWLTALX$^5$FLGX$^6$AAAX$^7$AXAX$^8$QXLSX$^9$L-amide
(X=L-2-aminoadipic acid (Aad), $X^5$ to $X^9$=homoarginine)

The most preferable peptides of the present invention are shown below.
HA/E2: IWLTALX$^5$FLGX$^6$AAAX$^7$AEAX$^8$QELSX$^9$L-amide
L17Aad: IWLTALX$^5$FLGX$^6$HAAX$^7$HXAX$^8$QQLSX$^9$L-amide
HAad: IWLTALX$^5$FLGX$^6$AAAX$^7$AXAX$^8$QXLSX$^9$L-amide (X=L-2-aminoadipic acid (Aad), $X^5$ to $X^9$=Lys (K))
HAad-homoR:
IWLTALX$^5$FLGX$^6$AAAX$^7$AXAX$^8$QXLSX$^9$L-amide
(X=L-2-aminoadipic acid (Aad), $X^5$ to $X^9$=homoarginine)

Each amino acid of the peptide of the present invention represented by one letter symbol may be an L-type amino acid or a D-type amino acid. When the peptide of the present invention contains a D-type amino acid, the number of D-type amino acids may be one, or two or more; however, it is preferable that all of the amino acids are L-type amino acids, or that all of the amino acids are D-type amino acids. G (Gly) does not have an asymmetric carbon, and is thus treated as an L-type amino acid in the present specification.

The peptide of the present invention can efficiently release a target substance from endosomes to the cytoplasm.

When $R^1$ is a hydrogen atom, the N-terminal is an amino group ($NH_2$). When $R^1$ is an alkyl group, an acyl group, an alkoxycarbonyl group, an aralkyloxycarbonyl group, or an aryloxycarbonyl group, the N-terminal is monoalkylamino or acylamino, or urethane, such as alkoxycarbonylamino, aralkyloxycarbonylamino, or aryloxycarbonylamino.

The N-terminal of the peptide of the present invention may be a dialkylamino group substituted with two alkyl groups.

When $R^2$ is a hydroxyl group (OH), the C-terminal is a carboxyl group (COOH). When $R^2$ is an amino group ($NH_2$), the C-terminal is an amide group ($CONH_2$).

$R^1$ is preferably a hydrogen atom (H), an alkyl group, an alkoxycarbonyl group, or an acyl group; and more preferably a hydrogen atom.

$R^2$ is preferably a hydroxyl group (OH), an alkoxy group, or an amino group ($NH_2$).

Examples of alkyl groups include linear or branched $C_{1-6}$ alkyl groups, such as methyl, ethyl, n-propyl, isopropyl, n-butyl, isobutyl, sec-butyl, tert-butyl, pentyl, and hexyl.

Examples of monoalkylamino groups include amino groups substituted with a linear or branched $C_{1-6}$ alkyl group, such as methylamino, ethylamino, n-propylamino, isopropylamino, n-butylamino, isobutylamino, sec-butylamino, tert-butylamino, pentylamino, and hexylamino.

Examples of dialkylamino groups include amino groups disubstituted with a linear or branched $C_{1-6}$ alkyl group, such as dimethylamino, diethylamino, di-n-propylamino, diisopropylamino, di-n-butylamino, diisobutylamino, di-sec-butylamino, di-tert-butylamino, dipentylamino, and dihexylamino.

Examples of acyl groups include $C_{2-22}$, preferably $C_{2-18}$, linear or branched acyl groups, such as acetyl, propionyl, butyryl, isobutyryl, valeryl, isovaleryl, pivaloyl, lauroyl, myristoyl, palmitoyl, stearoyl, isostearoyl, oleoyl, and linoleoyl. Further, acyl groups containing an aromatic group, such as 1-pyreneacetyl and 1-pyrenebutyryl, can also be used.

Examples of alkoxycarbonyl groups include cholesteryloxycarbonyl, tert-butyloxycarbonyl, phytosteryloxycarbonyl, stearyloxycarbonyl, palmityloxycarbonyl, 2-octyldodecyloxycarbonyl, and behenyloxycarbonyl groups.

Examples of aralkyloxycarbonyl groups include benzyloxycarbonyl, phenethyloxycarbonyl, fluorenylmethyloxycarbonyl, anthrylmethyloxycarbonyl, biphenylylmethyloxycarbonyl, tetrahydronaphthylmethyloxycarbonyl, chromanylmethyloxycarbonyl, 2,3-dihydro-1,4-dioxanaphthalenylmethyloxycarbonyl, indanylmethyloxycarbonyl, and phenanthrylmethyloxycarbonyl groups.

Examples of aryloxycarbonyl groups include fluorenyloxycarbonyl, phenyloxycarbonyl, naphthyloxycarbonyl, anthryloxycarbonyl, biphenylyloxycarbonyl, tetrahydronaphthyloxycarbonyl, chromanyloxycarbonyl, 2,3-dihydro-1,4-dioxanaphthalenyloxycarbonyl, indanyloxycarbonyl, and phenanthryloxycarbonyl groups.

Examples of monoarylamino groups include phenylamino, naphthylamino, anthrylamino, biphenylylamino, tetrahydronaphthylamino, chromanylamino, fluorenylamino, 2,3-dihydro-1,4-dioxanaphthalenylamino, indanylamino, and phenanthrylamino.

Examples of monocycloalkylamino include $C_{3-8}$ cycloalkylaminos, such as cyclopropylamino, cyclobutylamino, cyclopentylamino, cyclohexylamino, cycloheptylamino, and cyclooctylamino.

An alkoxycarbonyl group, an aralkyloxycarbonyl group, or an aryloxycarbonyl group may be directly bonded to the peptide of the present invention; however, these groups may be bonded to the peptide of the present invention via a suitable spacer, such as PEG (polyethylene glycol), an amide group (—CONH—, —NHCO—), an ester group (—COO—, —O—CO—), an ether group (—O—), an amino group (—NH—), alkylene (methylene, ethylene, propylene, butylene, pentylene, hexylene, etc.), or an amino acid (e.g., 20 natural amino acids). For example, a cholesteryl group or a phospholipid (e.g., phosphatidylethanolamine) may be bonded to the peptide of the present invention via a spacer, and the bound product may constitute a constituent of a vector, such as a liposome.

When $R^2$ is a hydroxyl group, the C-terminal is COOH. When $R^2$ is an amino group, the C-terminal is $CONH_2$. When $R^2$ is alkoxy, aralkyloxy, or aryloxy, the C-terminal is a corresponding ester. When $R^2$ is a monoalkylamino group, a monoarylamino group, monocycloalkylamino, or a dialkylamino group, the C-terminal is a corresponding amide.

Examples of alkoxy groups include cholesteryloxy, phytosteryloxy, stearyloxy, palmityloxy, 2-octyldodecyloxy, and behenyloxy groups.

Examples of aralkyloxy groups include benzyloxy, phenethyloxy, fluorenylmethyloxy, anthrylmethyloxy, biphenylylmethyloxy, tetrahydronaphthylmethyloxy, chromanylmethyloxy, 2,3-dihydro-1,4-dioxanaphthalenylmethyloxy, indanylmethyloxy, and phenanthrylmethyloxy groups.

Examples of aryloxy groups include fluorenyloxy, phenyloxy, naphthyloxy, anthryloxy, biphenylyloxy, tetrahydronaphthyloxy, chromanyloxy, 2,3-dihydro-1,4-dioxanaphthalenyloxy, indanyloxy, and phenanthryloxy groups.

Examples of target substances to be delivered to the cytoplasm include physiologically active substances, such as proteins, peptides, nucleic acids, drugs, sugars, and labeled substances thereof; as well as synthetic polymers, liposomes, and organic/inorganic/semiconductor particles. The physiologically active substances, such as proteins, peptides, nucleic acids, drugs, sugars, and labeled substances thereof; as well as synthetic polymers, liposomes, and organic/inorganic/semiconductor particles, may be bonded to the N-terminal or C-terminal of a peptide portion represented by $IWLTALX^5FLGX^6X^1AAX^7X^2X^3AX^8QX^4LSX^9L$ via a suitable spacer. Moreover, the physiologically active substances may be directly bonded to the N-terminal or C-terminal of the peptide portion represented by $IWLTALX^5FLGX^6X^1AAX^7X^2X^3AX^8QX^4LSX^9L$ without a spacer.

The peptides of the present invention wherein one or both of $R^1$ and $R^2$ are target substances may include the following:
(Physiologically active substance)-$IWLTALX^5FLGX^6X^1AAX^7X^2X^3AX^8QX^4LSX^9L$-(physiologically active substance);
(Physiologically active substance)-(spacer)-$IWLTALX^5FLGX^6X^1AAX^7X^2X^3AX^8QX^4LSX^9L$-(spacer)-(physiologically active substance);
(Physiologically active substance)-(spacer)-$IWLTALX^5FLGX^6X^1AAX^7X^2X^3AX^8QX^4LSX^9L$-(physiologically active substance);
(Physiologically active substance)-$IWLTALX^5FLGX^6X^1AAX^7X^2X^3AX^8QX^4LSX^9L$-(spacer)-(physiologically active substance);
(Physiologically active substance)-(spacer)-$IWLTALX^5FLGX^6X^1AAX^7X^2X^3AX^8QX^4LSX^9L$-$R^2$ ($R^2 \neq$ target substance);
$R^1$-$IWLTALX^5FLGX^6X^1AAX^7X^2X^3AX^8QX^4LSX^9L$-(spacer)-(physiologically active substance) ($R^1 \neq$ target substance);
(Physiologically active substance)-$IWLTALX^5FLGX^6X^1AAX^7X^2X^3AX^8QX^4LSX^9L$-$R^2$ ($R^2 \neq$ target substance); and
$R^1$-$IWLTALX^5FLGX^6X^1AAX^7X^2X^3AX^8QX^4LSX^9L$-(physiologically active substance) ($R^1 \neq$ target substance);
wherein $X^1$, $X^2$, $X^3$, $X^4$, $X^5$, $X^6$, $X^7$, $X^8$, and $X^9$ are as defined above; and $R^1$ and $R^2$ are as defined above, other than target substances.

Examples of proteins include antibodies, enzymes, cell signaling factors, transcription factors, DNA- or RNA-binding proteins; structural proteins in organelles, such as nucleus, mitochondria, and cytoskeleton; ubiquitin-proteasome-related proteins, such as ubiquitin and heat-shock proteins; apoptosis-related proteins, such as caspase; cell cycle-regulating proteins, such as p53; lectin; and the like. Other examples include proteins having gene-cutting/recombination ability, such as Cre reconbinase, TALEN, and Cas9. Examples of antibodies include immunoglobulins, fragment proteins thereof, and single-stranded antibodies derived from Camelidae animals. Examples of targets of these antibodies include kinases; transcription factors, such as HIF-1; cytoskeletal proteins, such as microtubules; and the like. Examples of peptides include helix peptides and cyclic peptides that regulate intracellular protein interaction, fragment peptides of intracellular proteins, DNA/RNA-binding peptides, various enzyme substrates and inhibitors, and antigen peptides for producing cancer vaccines, and the like. Examples of drugs include antitumor agents, antiviral agents, and the like. Examples of sugars include dextran, sialic acid, and the like. Examples of nucleic acids include DNA, RNA (preferably siRNA, miRNA, shRNA, rRNA, ribozyme, antisense RNA, etc.), DNA/RNA aptamers, and chemically modified products thereof. Further, the physiologically active substances also include composites of proteins and nucleic acids, such as Cas9/sgRNA. Moreover, in order to enhance intracellular physiological activity and function, it is also possible to introduce derivatives obtained by optionally chemically modifying the above physiologically active substances into cells as target substances.

Examples of the target substances also include products obtained by modifying physiologically active substances, such as the proteins and nucleic acids mentioned above, with fluorophores, quantum dots, radioactive isotopes, fluorescent proteins, luciferase, photocrosslinking groups, or the like for intracellular visualization, measurement, and interaction analysis; and stable isotope-labeled proteins for intracellular NMR measurement or the like. As the fluorophore, a fluorophore whose fluorescent properties change depending on the intracellular environment can be used for modification, if necessary.

The target substances to be introduced into cells are not necessarily limited to those described above. The present invention can also be used in combination with membrane-permeable peptides and other cell introduction agents, such as various transfection reagents, to further enhance intracytoplasmic transfer efficiency.

The peptide of the present invention wherein both of $R^1$ and $R^2$ are not target substances may be administered, as a composition, preferably as a pharmaceutical composition, in combination with the target substance, to vertebrates, preferably mammals including humans. When the target substance is not bonded to the peptide of the present invention, the target substance is constituted from a protein, a peptide, a nucleic acid, a drug, a sugar, or a labeled substance thereof; a synthetic polymer, a liposome, organic/inorganic/semiconductor particulates, or the like. A spacer is not contained.

In the composition or pharmaceutical composition comprising the peptide of the present invention and a target substance, the peptide of the present invention is contained in an amount of 1 to 10000 parts by mass, preferably 5 to 200 parts by mass, and more preferably 10 to 200 parts by mass, based on 100 parts by mass of the target substance.

The peptide of the present invention may be covalently bonded to a target substance directly or via a suitable spacer, or may be non-covalently bonded directly or via another molecule that interacts with the target substance to form a composite. Further, the peptide of the present invention may be contained in a vector (cell introduction agent) to be encapsulated by endosomes. For example, the peptide of the present invention may be contained inside the vector, or may be bonded to a constituent of the vector directly or via a spacer. Alternatively, the peptide of the present invention may non-covalently form a composite via another molecule that interacts with the constituent of the vector to be contained in the surface of the vector. Further, the peptide of the present invention and a target substance can be encapsulated inside the vector, and after the target substance is incorporated into endosomes, the transfer from the endosomes to the cytoplasm can be promoted. A composite in which the peptide of the present invention and a target substance are non-covalently bonded is included in the composition or pharmaceutical composition of the present invention.

The peptide of the present invention may be in the form of a dimer or multimer. The dimer or multimer is represented, for example, by the following formula (IA):

$$R^1\text{-(IWLTALX}^5\text{FLGX}^6\text{X}^1\text{AAX}^7\text{X}^2\text{X}^3\text{AX}^8\text{QX}^4\text{LSX}^9\text{L-Y)}_n\text{-R}^2 \quad (IA)$$

wherein $R^1$, $R^2$, $X^1$, $X^2$, $X^3$, $X^4$, $X^5$, $X^6$, $X^7$, $X^8$, and $X^9$ are as defined above; Y represents a single bond or a spacer; and n is 2, 3, 4, 5, 6, 7, 8, 9 or 10, preferably an integer of 2 to 6, and more preferably an integer of 2 to 4.

In the present specification, examples of spacers include ester bonds (—CO—O—, —O—CO—), ether bonds (—O—), amide bonds (NHCO, CONH), sugar chain linkers, polyethylene glycol linkers, peptide linkers, and the like. Examples of peptide linkers include linkers containing at least one of 20 natural amino acids that constitute a protein. The number of amino acids of the peptide linker is, for example, but not limited to, 1 to 20, 1 to 15, 1 to 12, 1 to 10, 1 to 8, 1 to 6, or 1 to 4. Examples of peptide linkers include arginine dimer, arginine trimer, arginine tetramer, lysine dimer, lysine trimer, lysine tetramer, glycine dimer, glycine trimer, glycine tetramer, glycine pentamer, glycine hexamer, alanine-alanine-tyrosine (AAY), isoleucine-leucine-alanine (ILA), arginine-valine-lysine-arginine (RVKR), and the like. The spacer may be divalent or multivalent.

When the peptide of the present invention is a multimer, a branched multivalent linker (e.g., dendrimer), a metal complex, or the like may be used for linkage. The dendrimer is represented, for example, by the following formula (IB):

$$Z\text{—}(R^a)_m \quad (IB)$$

wherein Z represents a branched multivalent linker; $R^a$ is the same or different, and each represents:

$R^1$-IWLTALX$^5$FLGX$^6$X$^1$AAX$^7$X$^2$X$^3$AX$^8$QX$^4$LSX$^9$L-Y-, or

Y-IWLTALX$^5$FLGX$^6$X$^1$AAX$^7$X$^2$X$^3$AX$^8$QX$^4$LSX$^9$L-R$^2$, wherein $R^1$, $R^2$, $X^1$, $X^2$, $X^3$, $X^4$, $X^5$, $X^6$, $X^7$, $X^8$, $X^9$, and Y are as defined above; and m is 3, 4, or 5.

Examples of the branched multivalent linker represented by Z include diethylenetriamine, spermine, spermidine, triethanolamine, ethylenediaminetetraacetate (EDTA), pentaerythritol, azido-propyl(alkyl)amine, lysine, ornithine, asparagic acid, glutamic acid, polyfunctional peptides (lysine, ornithine, or asparagic acid- or glutamic acid-containing dipeptide, tripeptide, or tetrapeptide), and organic multivalent amino compounds (e.g., poly(amidoamine) (PAMAM), tris(ethyleneamine)ammonia, and poly(propyleneimine) (Astramol (trademark))). m is an integer of 2 to 8, preferably an integer of 2 to 6, and more preferably an integer of 2 to 4, for example, 3 or 4. The dendrimer of the present invention includes, for example, a dimer obtained by connecting the N-terminals (or C-terminals) of peptides represented by IWLTALX$^5$FLGX$^6$X$^1$AAX$^7$X$^2$X$^3$AX$^8$QXLSX$^9$L. Further, the dendrimer of the present invention also includes a tetramer obtained by further connecting a "dimer obtained by connecting the N-terminals of the above peptides" and a "dimer obtained by connecting the C-terminals of the above peptides."

When the peptide of the present invention is allowed to coexist with a target substance, the transfer of the target substance from endosomes to the cytoplasm can be promoted; however, there is no specificity for introduction into specific cells. Therefore, the peptide of the present invention and the target substance are delivered to target cells by DDS, or the peptide of the present invention is combined with a cell-specific vector, whereby the target substance can be introduced into the cytoplasm of specific cells. Examples of cell-specific vectors include vectors in which cell-specific antibodies, ligands, etc., are introduced into their surfaces. Examples of vectors include liposomes (cationic liposomes, anionic liposomes), lipid microspheres, Lipofectamine, polymer micelles comprising a block copolymer containing a hydrophilic segment and an inner core-forming segment (a hydrophobic segment, a cationic segment, a metal complex-forming segment, etc.), polymer hollow carriers (e.g., the drug carrier containing a polysarcosine derivative described in JP5142313B, and the electrostatic coupling type polymer micelle comprising a block copolymer having a non-chargeable segment and a chargeable segment described in WO2004/105799), nanogels, high-density lipoproteins (HDL), synthetic polymers, nanoparticles, and the like. Self-assembled nucleic acid-derived vectors and virus outer shell protein-derived vectors may also be used. For example, when the vector is a liposome, a liposome containing the peptide of the present invention can be obtained by binding the peptide of the present invention with an acyl group having 10 or more carbon atoms as $R^1$, or with a highly lipophilic group, such as a group having a cholesteryloxycarbonyl group at the N-terminal or a cholesteryl group at the C-terminal, or a phospholipid, such as phosphatidylethanolamine, via an ester bond or an amide, optionally via a suitable spacer. Examples of spacers include PEG (polyethylene glycol), amide groups (—CONH—, —NHCO—), ester groups (—COO—, —O—CO—), ether groups (—O—), amino groups (—NH—), alkylenes (e.g., methylene, ethylene, propylene, butylene, pentylene, and hexylene), amino acids, and the like. The amino acid may be bonded via COOH or NH$_2$ of the side chain. Examples of virus (outer shell protein)-derived vectors include retroviral vectors, adenoviral vectors, Sendai-virus vectors, and the like. Examples of self-assembled nucleic acid-derived vectors include those described in WO2012144560A1 and WO2016/006628. It is also possible to enhance the effect of destabilizing the endosomal membrane and the effect of delivering a target substance to the cytoplasm by conjugating the peptide of the present invention and a "molecule that enhances the affinity of the peptide of the present invention to a target cell" to thereby more efficiently/effectively transfer and store the peptide of the present invention in the endosomes of the cell. Examples of the "molecule that enhances the affinity of the peptide of the present invention to a target cell" include ligands binding to receptors present on cell surfaces (folate receptors, transferrin receptors, receptors of sugars, such as glucose; and receptors of growth factors, such as epidermal growth factor (EGF) and vessel endothelial growth factor (VEGF)), fatty acids, hydrophobic peptides, basic peptides (e.g., polyarginine), sugar chains, and the like.

Further, the peptide of the present invention and a target substance can form a non-covalently bonded composite directly or via another molecule that interacts with the target substance. Examples of such non-covalently bonded composites include:
(a) a composite of [a conjugate of the peptide of the present invention and a peptide with affinity to an antibody (selected using a phage display system etc.)] and the antibody;
(b) a non-covalently bonded composite of a nucleic acid and the peptide of the present invention; and
(c) a non-covalently bonded composite of [a conjugate of the peptide of the present invention and a nucleic acid-interacting molecule] and a nucleic acid.

The organism species in which target substances are to be delivered to their cells are vertebrates, and preferably mammals. Examples of mammals include humans, monkeys, cows, sheep, goats, horses, pigs, rabbits, dogs, cats, rats, mice, guinea pigs, and the like.

EXAMPLES

The present invention is described below in more detail with reference to Examples. However, the scope of the invention is not limited to these Examples.

Example 1

1. Structure and Production of Peptides
L17E (L17):
IWLTALX$^5$FLGX$^6$HAAX$^7$HEAX$^8$QQLSX$^9$L-amide (SEQ ID NO: 1, R1=H, R2=NH2)
L17E/Q21E (L17Q21):
IWLTALX$^5$FLGX$^6$HAAX$^7$HEAX$^8$QELSX$^9$L-amide (SEQ ID NO: 2, R1=H, R2=NH2)

HA/E2:
R$^1$-IWLTALX$^5$FLGX$^6$AAAX$^7$AEAX$^8$QELSX$^9$L-R$^2$ (I-6)

L17Aad:
R$^1$—IWLTALX$^5$FLGX$^6$HAAX$^7$HXAX$^8$QQLSX$^9$L-R$^2$ (I-3)

HAad:
R$^1$-IWLTALX$^5$FLGX$^6$AAAX$^7$AXAX$^8$QXLSX$^9$L-R$^2$ (I-17)

HA/E1:
R$^1$—IWLTALX$^5$FLGX$^6$AAAX$^7$AEAX$^8$QQLSX$^9$L-R$^2$ (I-5)

L17Aad/Q2 Aad:
R$^1$-IWLTALX$^5$FLGX$^6$HAAX$^7$HXAX$^8$QXLSX$^9$L-R$^2$ (I-11)

(wherein R$^1$ is H, R$^2$ is NH$_2$, X is L-2-aminoadipic acid (Aad), and X$^5$ to X$^9$ are Lys(K)).

Peptides that selectively destabilize endosomal membranes were obtained by substituting amino acids at positions 12, 16, 17, and/or 21 in the sequence of L17E described in the Examples of PTL 2. The peptides were obtained by solid-phase synthesis. The physical property values of the obtained peptides are shown below.
Physical Property Value of L17E (L17) (MALDI-TOFMS):
 theoretical value (M+H)$^+$ 2860.6; measured value 2860.5.
Physical Property Value of L17E/Q21E:
 theoretical value (M+H)$^+$ 2861.4; measured value 2860.4.
Physical Property Value of HA/E2:
 theoretical value (M+H)$^+$ 2727.6; measured value 2727.4.
Physical Property Value of L17Aad:
 theoretical value (M+H)$^+$ 2873.7; measured value 2873.5.
Physical Property Values of HAad:
 theoretical value (M+H)$^+$ 2755.7; measured value 2755.6.
Physical Property Values of HA/E1:
 theoretical value (M+H)$^+$ 2726.6; measured value 2726.2.
Physical Property Values of L17Aad/Q21Aad:
 theoretical value (M+H)$^+$ 2887.7; measured value 2886.7.

Example 2: Helix Content

The helix content of the peptides obtained in Example 1 (L17E, L17E/Q21E, L17Aad, HA/E1, HA/E2, and HAad) was calculated in the presence of POPC/POPG (3:1) liposomes by the method of Y. H. Chen et al., 1972, based on 222-nm molar ellipticity ($[\theta]_{222}$) using the following formula:

Helix content (%)=−($[\theta]_{222}$+2340)/30300*100.

Figure 1:
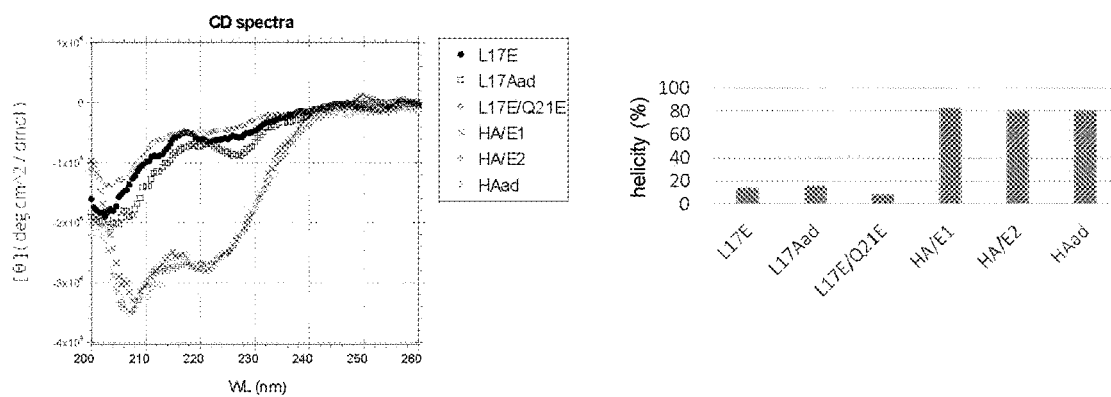
FIG. 1 shows the CD spectra of peptides in the presence of POPC/POPG (3:1) liposomes (left), and helicity (right). The helix content was calculated by the method of Y. H. Chen et al., 1972, based on 222-nm molar ellipticity ($[\theta]_{222}$) using the following formula.

Further, the CD spectra of the peptides were measured. FIG. 1 shows the CD spectra (left) and helix content (right).

Example 3: Intracellular Introduction (1) of Macromolecular Drug Model (10 kDa Dextran)

In the presence of each peptide obtained in Example 1 (L17E, L17E/Q21E, HA/E1, HA/E2) (40 μM) or in the absence of the peptides (a control, no peptide), HeLa cells and Alexa 488-dextran (Molecular Probes, 10 kDa) (200 μg/mL) were treated in α-MEM(−) for 1 hour. The cells were washed, and observed with a confocal microscope. FIG. 2 shows the results.

Significant outflow of Alexa 488-dextran (10 kDa) into the cytoplasm and diffusion therein were observed in the presence of the peptides of the present invention.

Example 4: Intracellular Introduction (2) of Macromolecular Drug Model (10 kDa Dextran)

In the presence of each peptide obtained in Example 1 (L17E, L17Aad) (40 μM) or in the absence of the peptides (a control, no peptide), HeLa cells and Alexa 488-dextran (Molecular Probes, 10 kDa) (200 μg/mL) were treated in α-MEM(−) for 1 hour. The cells were washed, and observed with a confocal microscope. FIG. 3 shows the results.

Significant outflow of Alexa 488-dextran (10 kDa) into the cytoplasm and diffusion therein were observed in the presence of the peptide of the present invention (L17Aad), as compared with the levels of outflow and diffusion in the presence of known L17E.

Example 5: Intracellular Introduction (3) of Macromolecular Drug Model (10 kDa Dextran)

In the presence of each peptide obtained in Example 1 (HAad, HA/E2, L17Aad, L17E) (40 μM) or in the absence of the peptides (a control, no peptide), HeLa cells and Alexa 488-dextran (Molecular Probes, 10 kDa) (200 μg/mL) were treated in α-MEM(−) for 1 hour. The cells were washed, and observed with a confocal microscope. FIG. 4 shows the results.

Significant outflow of Alexa 488-dextran (10 kDa) into the cytoplasm and diffusion therein were observed in the presence of the peptides of the present invention (HAad, HA/E2, and 17Aad), as compared with the levels of outflow and diffusion in the presence of known L17E.

Example 6: Comparison (1) of Efficiency of Intracellular Release of Dextran (10 kDa)

When HeLa cells were incubated with Alexa 488-dextran (10 kDa) (200 μg/mL) as a macromolecular drug model in the presence of HAad (40 μM) in α-MEM(−) for 1 hour, Alexa 488-dextran release into about 75% of cells (cytosol) was observed. In contrast, when the incubation was performed in the presence of L17E, Alexa 488-dextran release into about 50% of the cells was observed.

With respect to the peptide concentration required to detect the signal of intracellularly released Alexa 488-dextran in 50% of the cells, the concentration of L17E was 40 μM, and the concentration of HAad was 20 μM ($EC_{50}$ is ½).

Example 7: Comparison (2) of Efficiency of Intracellular Release of Dextran (10 kDa)

Intracellular release of dextran is more difficult in NIH3T3 cells than in HeLa cells. NIH3T3 cells and dextran (10 kDa) were incubated in the presence of HAad, HA/E2, or L17E (40 μM each) in DEME(−) medium for 1 hour in the same manner as in Example 6. Intracellular release of dextran was observed in about 35%, 25%, and 17% of the cells in the presence of HAad, HA/E2, and L17E, respectively (the intracellular release achieved by HAad treatment was twice the release achieved by L17E).

Example 8: Comparison (1) of Efficiency of Intracellular Release of Human Immunoglobulin (IgG, Circa 160 kDa)

The cells and human immunoglobulin fluorescently labeled with Alexa 488 (IgG, circa 160 kDa) (500 μg/mL) were incubated in the presence of HAad, HA/E2, or L17E (40 μM each) in α-MEM(−) medium for 1 hour in the same manner as in Example 6. Intracellular release of human immunoglobulin was observed in about 70%, 45%, and 35% of the entire cells in the presence of HAad, HA/E2, and L17E, respectively (in FIG. 7, the intracellular release achieved by HAad treatment was twice the release achieved by L17E).

Example 9: Comparison (2) of Efficiency of Intracellular Release of Human Immunoglobulin (IgG, Circa 160 kDa)

In Example 8, HAad was confirmed to have a high ability to intracellularly release endosome-encapsulated IgG. Based on this confirmation, whether the IgG dose to be administered can be reduced was investigated.

The cells and human immunoglobulin fluorescently labeled with Alexa 488 (IgG, circa 160 kDa) (50 μg/mL: ⅒ the volume of Example 8) were incubated in the presence of HAad or L17E (40 μM each) in α-MEM(−) medium for 1 hour. When the cells were treated with HAad, intracellular release of human immunoglobulin was observed in 50% of the entire cells. In contrast, when the cells were treated with L17E, the release was observed in only about 10% of the cells (in FIG. 8, the intracellular release achieved by HAad treatment was 5 times the release achieved by L17E; and the IgG dose required for intracellular IgG release in 50% of the cells was ⅒).

Example 10: Comparison (3) of Efficiency of Intracellular Release of Human Immunoglobulin (IgG, Circa 60 kDa)

In Examples 8 and 9, HAad was confirmed to have high ability to intracellularly release endosome-encapsulated IgG, even at a reduced IgG dose. Based on this confirmation, whether the amount of peptide to be administered can be reduced was investigated.

In the presence of HAad or L17E (20 μM each: ½ the amount used in Examples 8 and 9), the cells and human immunoglobulin fluorescently labeled with Alexa 488 (IgG, circa 160 kDa) (500 μg/mL: the same amount as in Example 8) were incubated in α-MEM(−) medium for 1 hour. When the cells were treated with 20 μM HAad, intracellular release of human immunoglobulin was observed in about 37% of the entire cells. When the cells were treated with L17E, the release was observed in only about 15% of the cells. (In FIG. 9, the intracellular release achieved by treatment with a low concentration of HAad was 2.5 times the release achieved by L17E. With respect to the peptide concentration required to detect the signal of intracellularly released human immunoglobulin in 35% of the cells, the concentration of L17E is 40 μM, and the concentration of HAad is 20 μM, which is half the concentration of L17E.)

Example 11: Cell-Killing Assay by Intracellular Delivery of Toxin Protein Saporin Saporin is known as a cytotoxin that kills cancer cells by its intracellular delivery. RAW 264.7 cells and saporin (10 μg/mL) were incubated in the presence of HAad, HA/E2, or L17E (40 μM each) in α-MEM(−) medium for 1 hour. After the cells were then washed and the medium was replaced with DMEM(+), the cells were further incubated for 6 hours. The cell viability (%) was assayed by WST-8 assay (FIG. 10). The results show that the viability (%) of the cells achieved by the treatment of saporin in the presence of HAad and HA/E2 was 4% and 6%, respectively, which are significantly reduced values as compared with the cell viability (%) in the presence of L17E (16%); and that the viability (%) in the presence of HAad was ¼ the viability (%) in the presence of L17E.

Example 12: Genetic Recombination Assay by Intracellular Delivery of Cre Protein HeLa cells transfected with a plasmid encoding loxP-DsRed-loxP-EGFP, which were prepared in the same manner as in the Examples of PTL 2, were incubated with His-tag fusion Cre (Cre-Hiss) (10 μM) in the presence of HAad, HA/E2, or L17E (40 μM each) for 1 hour. This system was designed to express EGFP when intracellular release of Cre protein induces genetic recombination. After the cells were washed and cultured in α-MEM(+) for 24 hours, the cells were observed with a confocal microscope (FIG. 11). The proportions of EGFP-expressing cells in the peptide-treated cell groups were significantly increased as compared with that in a control cell group (to which only Cre-His$_6$ was administered). The proportions of GFP-expressing cells in the cells treated with HAad, HA/E2, and L17E were 41%, 36%, and 30%, respectively. Considering the fact that the EGFP expression efficiency achieved with no administration of a release peptide was 9%, peptide administration of HAad, HA/E2, and L17E can be considered to increase genetic recombination by 32%, 27%, and 22%, respectively, as compared with no peptide administration. Genetic recombination was more significantly promoted by administration of HAad than by administration of L17E.

Example 13: Mitochondrial Damage by Peptide Treatment

Mitochondrial membranes are considered to be rich in acidic lipid, as compared with cell membranes. Accordingly, the effects of the above peptides on a mitochondrial membrane were examined by JC-1 assay. A JC-1 reagent emits red (J-aggregate) fluorescence when the mitochondrial membrane is kept normal and the membrane potential is maintained; and the JC-1 reagent emits green (J-monomer) fluorescence when the mitochondrial membrane is damaged and the membrane potential is not kept normal. After HeLa cells were incubated with HAad, HA/E2, or L17E (40 μM) in α-MEM(−) for 1 hour, JC-1 assay was performed. The percentage of cells that emitted red fluorescence was assayed by flow cytometry. The effects of an uncoupling agent that inhibits ATP synthesis (carbonyl cyanide-p-trifluoromethoxyphenylhydrazone, FCCP) (40 μM, incubation in α-MEM(−) for 1 hour) and a complex of a pCI vector (an empty vector) with Lipofectamine LTX, which is a cationic gene transfection reagent (overnight incubation in α-MEM (+) according to the standard protocol) were also examined in a similar manner (FIG. 12).

The following results were obtained. Most of the cells treated with FCCP changed to emit green fluorescence. On the other hand, when the cells were treated with L17E, the percentage of cells that showed a red color decreased slightly, as compared with the percentage achieved when the cells were untreated with a peptide. In contrast, when the cells were treated with HA/E2 or HAad, there was no significant difference from the untreated case. The results thus suggest that these peptides had little effect on the mitochondrial membrane, and damage by HA/E2 or HAad is even less than that by L17E. The results show that although commonly used Lipofectamine has slight mitochondrial damage activity, the peptides of the present invention, HA/E2 and HAad, do not damage mitochondria.

Example 14: Nuclear Accumulation of Nuclear Localization Signal Fusion Green Fluorescent Protein (NLS-EGFP)

The cells and NLS-EGFP (10 μM) were incubated in the presence of HAad or L17E (40 μM each) in α-MEM(−) medium for 1 hour in the same manner as in Example 6. If NLS-EGFP is intracellularly released while maintaining its activity, localization of green fluorescence in the nuclei is observed. The results show that localization of NLS-EGFP in the nuclei was observed in about 84% and 56% of the entire cells in the presence of HAad and L17E, respectively (FIG. 13). A high activity of HAad to release endosome-encapsulated substances was also confirmed in this system.

Example 15: Evaluation of Cell Viability (%) 24 Hours after Peptide Treatment in the Presence of Serum After the cells were incubated in the presence of HAad, HA/E2, or L17E (each 10 μM, 20 μM, and 40 μM) in α-MEM(+) medium for 24 hours, the cell viability (%) was evaluated by WST-8 assay (FIG. 14). The cell viability (%) after 24 hours with the use of any peptide at any concentration was almost 100%. Thus, no significant toxicity was observed in HA/E2 and HAad, as in L17E.

Example 16

1) Preparation of H-IWLTALZFLGZAAAZAX-AZQXLSZL-amide (SEQ ID NO: 11) (HAad-homoR) (wherein Z=homoarginine, and X=L-2-aminoadipic acid)

The title compound was synthesized according to Francesco L. Brancia et al., Anal. Chem., 2004, 76 (10), 2748-2755. Aqueous ammonia was added to an aqueous solution of O-methylisourea hemisulfate (1.23 g) to adjust the pH to 11.0. An aqueous solution of HAad (H-IWLTALKFLG-KAAAKAXAKQXLSKL-amide) (SEQ ID NO: 12) (1.3 mM, 38 μL) was added thereto to achieve a final O-methylisourea hemisulfate concentration of 0.5M and a final 1c concentration of 5 μM, respectively and to make a total volume of 10 mL. A reaction was allowed to proceed at room temperature overnight. After the reaction was stopped by adding the same volume of a 1% aqueous trifluoroacetic acid solution, the resulting mixture was lyophilized and purified by reverse-phase HPLC. Mass spectrometry (MALDI TOFMS) confirmed that the desired product was obtained (measured value 2965.8; theoretical value 2965.8 (M+H)$^+$).

2) Release activity of H-IWLTALZFLGZAAAZAX-AZQXLSZL-amide (SEQ ID NO: 11) to release Alexa 488-dextran (10 kDa) into the cytoplasm HeLa cells, Alexa 488-dextran (Molecular Probes, 10 kDa) (200 μg/mL), and HAad; or HeLa cells, Alexa 488-dextran, (Molecular Probes, 10 kDa) (200 μg/mL), and HAad-homoR (20 μM) were treated in α-MEM(−) for 1 hour. The cells were washed, and observed with a confocal microscope. The release of Alexa 488-dextran into the cytoplasm was observed in 75% of the HAad-homoR-treated cells, whereas the release was observed in about 40% of the HAad-treated cells.

The results clarify that formation of homoarginine by converting amino groups of five Lys(K) residues to guanidino groups can significantly increase the release activity of the intracellularly introduced protein into the cytoplasm.

INDUSTRIAL APPLICABILITY

1. Reagents and Kits for Introducing Proteins and Physiologically Active Substances into Living Cells
2. Basic Research in the Fields of Molecular Cell Biology and Medicine (Intracellular Visualization, Measurement, Interaction Analysis, Cell Activity Control, Etc.)
3. Basic Research for the Evaluation of Intracellular Activities of Antibody Drugs and Biopharmaceuticals in the Field of Drug Discovery (Biopharmaceutical Design Support Method)
4. Ex Vivo/In Vivo Intracellular Delivery of Antibody Drugs, Nucleic Acid Drugs, and Biopharmaceuticals

The invention claimed is:

1. A peptide represented by any one of the following formulas:

$$R^1\text{-IWLTALX}^5\text{FLGX}^6\text{AAAX}^7\text{AEAX}^8\text{QELSX}^9\text{L-R}^2, \quad (Ia)$$

$$R^1\text{-IWLTALX}^5\text{FLGX}^6\text{AAAX}^7\text{AXAX}^8\text{QXLSX}^9\text{L-R}^2, \quad (Ic)$$

and $$R^1\text{-IWLTALX}^5\text{FLGX}^6\text{AAAX}^7\text{AEAX}^8\text{QQLSX}^9\text{L-R}^2; \quad (Id)$$

wherein X represents L-2-aminoadipic acid (Aad), 2-aminopimelic acid, or 2-aminosuberic acid;

$R^1$ represents a hydrogen atom, an alkyl group, an acyl group, an alkoxycarbonyl group, an aralkyloxycarbonyl group, an aryloxycarbonyl group, or a target substance;

$R^2$ represents a hydroxyl group (OH), an amino group (NH2), a monoalkylamino group, a monoarylamino group, monocycloalkylamino, a dialkylamino group, an alkoxy group, an aralkyloxy group, an aryloxy group, or a target substance; and $X^5$ to $X^9$ are the same or different, and each represents Lys (K), Arg (R), homoarginine, ornithine, homolysine, or 2-amino-7-guanidinoheptanoic acid.

2. The peptide according to claim 1 represented by any one of the following formulas:

$$R^1\text{-IWLTALX}^5\text{FLGX}^6\text{AAAX}^7\text{AEAX}^8\text{QELSX}^9\text{L-R}^2, \quad (Ia)$$

and $$R^1\text{-IWLTALX}^5\text{FLGX}^6\text{AAAX}^7\text{AXAX}^8\text{QXLSX}^9\text{L-R}^2; \quad (Ic)$$

wherein X represents L-2-aminoadipic acid (Aad), 2-aminopimelic acid, or 2-aminosuberic acid;

$R^1$ represents a hydrogen atom, an alkyl group, an acyl group, an alkoxycarbonyl group, an aralkyloxycarbonyl group, an aryloxycarbonyl group, or a target substance;

$R^2$ represents a hydroxyl group (OH), an amino group (NH2), a monoalkylamino group, a monoarylamino group, monocycloalkylamino, a dialkylamino group, an alkoxy group, an aralkyloxy group, an aryloxy group, or a target substance; and $X^5$ to $X^9$ are the same or different, and each represents Lys (K), Arg (R), homoarginine, ornithine, homolysine, or 2-amino-7-guanidinoheptanoic acid.

3. The peptide according to claim 1 represented by formula (Ic):

$$R^1\text{-IWLTALX}^5\text{FLGX}^6\text{AAAX}^7\text{AXAX}^8\text{QXLSX}^9\text{L-R}^2;\quad (Ic)$$

wherein X represents L-2-aminoadipic acid (Aad), 2-aminopimelic acid, or 2-aminosuberic acid;

$R^1$ represents a hydrogen atom, an alkyl group, an acyl group, an alkoxycarbonyl group, an aralkyloxycarbonyl group, an aryloxycarbonyl group, or a target substance;

$R^2$ represents a hydroxyl group (OH), an amino group (NH2), a monoalkylamino group, a monoarylamino group, monocycloalkylamino, a dialkylamino group, an alkoxy group, an aralkyloxy group, an aryloxy group, or a target substance; and $X^5$ to $X^9$ are the same or different, and each represents Lys (K), Arg (R), homoarginine, ornithine, homolysine, or 2-amino-7-guanidinoheptanoic acid.

4. A peptide represented by IWLTALKFLGKAAAKAX-AKQXLSKL-amide (SEQ ID NO: 12) (HAad), wherein X represents L-2-aminoadipic acid (Aad).

5. A cytoplasmic delivery agent comprising the peptide according to claim 1.

6. A cytoplasm-targeted substance-introducing agent comprising the peptide according to claim 1 in a vector.

7. A cytoplasm-targeted substance-introducing agent comprising the peptide according to claim 1; and a target substance covalently bonded directly or via a spacer to the peptide.

8. A cytoplasm-targeted substance-introducing agent comprising a composite having the peptide according to claim 1; and a target substance non-covalently bonded directly or via a molecule to the peptide, the molecule interacting with the target substance.

9. The cytoplasm-targeted substance-introducing agent according to claim 6, wherein a target substance is encapsulated in the vector.

10. The substance-introducing agent according to claim 6, wherein the peptide is bonded to a constituent of the vector directly or via a spacer.

11. The substance-introducing agent according to claim 5, comprising a conjugate of the peptide and a molecule that increases the affinity of the peptide to a target cell.

12. The substance-introducing agent according to claim 6, wherein the peptide is encapsulated in the vector, together with a target substance.

13. The substance-introducing agent according to claim 6, wherein the vector is a liposome, a lipid microsphere, a polymer micelle, a polymer hollow carrier, a nanogel, a high-density lipoprotein (HDL), a synthetic polymer, a self-assembled nucleic acid-derived vector, a virus outer shell protein-derived vector, or a nanoparticle.

14. The substance-introducing agent according to claim 10, wherein the constituent of the vector is cholesterol or a phospholipid, and the vector comprises a composite comprising cholesterol or a phospholipid, and the peptide.

* * * * *

SEQUENCE LISTING

<160> NUMBER OF SEQ ID NOS: 12

<210> SEQ ID NO 1
<211> LENGTH: 25
<212> TYPE: PRT
<213> ORGANISM: Lycosa carolinensis

<400> SEQUENCE: 1

Ile Trp Leu Thr Ala Leu Lys Phe Leu Gly Lys His Ala Ala Lys His
1               5                   10                  15

Glu Ala Lys Gln Gln Leu Ser Lys Leu
            20                  25

<210> SEQ ID NO 2
<211> LENGTH: 25
<212> TYPE: PRT
<213> ORGANISM: Lycosa carolinensis

<400> SEQUENCE: 2

Ile Trp Leu Thr Ala Leu Lys Phe Glu Gly Lys His Ala Ala Lys His
1               5                   10                  15

Leu Ala Lys Gln Gln Leu Ser Lys Leu
            20                  25

<210> SEQ ID NO 3
<211> LENGTH: 25
<212> TYPE: PRT
<213> ORGANISM: Lycosa carolinensis

<400> SEQUENCE: 3

Ile Trp Leu Thr Ala Leu Lys Phe Leu Gly Lys His Glu Ala Lys His
1               5                   10                  15

Leu Ala Lys Gln Gln Leu Ser Lys Leu
            20                  25

<210> SEQ ID NO 4
<211> LENGTH: 25
<212> TYPE: PRT
<213> ORGANISM: Lycosa carolinensis

<400> SEQUENCE: 4

Ile Trp Leu Thr Ala Leu Lys Phe Leu Gly Lys His Ala Ala Lys His
1               5                   10                  15

Glu Ala Lys Gln Gln Leu Ser Lys Leu
            20                  25

<210> SEQ ID NO 5
<211> LENGTH: 25
<212> TYPE: PRT
<213> ORGANISM: Lycosa carolinensis

<400> SEQUENCE: 5

Ile Trp Leu Thr Ala Leu Lys Phe Leu Gly Lys His Glu Ala Lys His
1               5                   10                  15

Glu Ala Lys Gln Gln Leu Ser Lys Leu
            20                  25

<210> SEQ ID NO 6
<211> LENGTH: 25
<212> TYPE: PRT
<213> ORGANISM: Lycosa carolinensis

<400> SEQUENCE: 6

```
Ile Trp Leu Thr Ala Leu Lys Phe Leu Gly Lys His Ala Ala Lys His
1               5                   10                  15

Glu Ala Lys Gln Glu Leu Ser Lys Leu
            20                  25

<210> SEQ ID NO 7
<211> LENGTH: 25
<212> TYPE: PRT
<213> ORGANISM: Lycosa carolinensis

<400> SEQUENCE: 7

Ile Trp Leu Thr Ala Leu Lys Phe Leu Gly Lys His Ala Ala Lys His
1               5                   10                  15

Asp Ala Lys Gln Gln Leu Ser Lys Leu
            20                  25

<210> SEQ ID NO 8
<211> LENGTH: 25
<212> TYPE: PRT
<213> ORGANISM: Lycosa carolinensis

<400> SEQUENCE: 8

Ile Trp Leu Thr Ala Leu Lys Phe Leu Gly Lys His Ala Ala Lys His
1               5                   10                  15

Glu Ala Lys Gln Gln Leu Ser Lys Leu
            20                  25

<210> SEQ ID NO 9
<211> LENGTH: 22
<212> TYPE: PRT
<213> ORGANISM: Lycosa carolinensis

<400> SEQUENCE: 9

Ile Trp Leu Thr Ala Leu Lys Phe Leu Gly Lys His Ala Ala Lys His
1               5                   10                  15

Glu Ala Lys Gln Gln Leu
            20

<210> SEQ ID NO 10
<211> LENGTH: 19
<212> TYPE: PRT
<213> ORGANISM: Lycosa carolinensis

<400> SEQUENCE: 10

Ile Trp Leu Thr Ala Leu Lys Phe Leu Gly Lys His Ala Ala Lys His
1               5                   10                  15

Glu Ala Lys

<210> SEQ ID NO 11
<211> LENGTH: 25
<212> TYPE: PRT
<213> ORGANISM: Lycosa carolinensis
<220> FEATURE:
<221> NAME/KEY: MISC_FEATURE
<222> LOCATION: (7)..(7)
<223> OTHER INFORMATION: Xaa is homoarginin
<220> FEATURE:
<221> NAME/KEY: MISC_FEATURE
<222> LOCATION: (11)..(11)
<223> OTHER INFORMATION: Xaa is homoarginin
<220> FEATURE:
<221> NAME/KEY: MISC_FEATURE
<222> LOCATION: (15)..(15)
<223> OTHER INFORMATION: Xaa is homoarginin
```

```
<220> FEATURE:
<221> NAME/KEY: MISC_FEATURE
<222> LOCATION: (17)..(17)
<223> OTHER INFORMATION: Xaa is Aad
<220> FEATURE:
<221> NAME/KEY: MISC_FEATURE
<222> LOCATION: (19)..(19)
<223> OTHER INFORMATION: Xaa is homoarginine
<220> FEATURE:
<221> NAME/KEY: MISC_FEATURE
<222> LOCATION: (21)..(21)
<223> OTHER INFORMATION: Xaa is Aad
<220> FEATURE:
<221> NAME/KEY: MISC_FEATURE
<222> LOCATION: (24)..(24)
<223> OTHER INFORMATION: Xaa is homoarginine

<400> SEQUENCE: 11

Ile Trp Leu Thr Ala Leu Xaa Phe Leu Gly Xaa Ala Ala Ala Xaa Ala
1               5                   10                  15

Xaa Ala Xaa Gln Xaa Leu Ser Xaa Leu
            20                  25

<210> SEQ ID NO 12
<211> LENGTH: 25
<212> TYPE: PRT
<213> ORGANISM: Lycosa carolinensis
<220> FEATURE:
<221> NAME/KEY: MISC_FEATURE
<222> LOCATION: (17)..(17)
<223> OTHER INFORMATION: Xaa is Aad
<220> FEATURE:
<221> NAME/KEY: MISC_FEATURE
<222> LOCATION: (21)..(21)
<223> OTHER INFORMATION: Xaa is Aad

<400> SEQUENCE: 12

Ile Trp Leu Thr Ala Leu Lys Phe Leu Gly Lys Ala Ala Ala Lys Ala
1               5                   10                  15

Xaa Ala Lys Gln Xaa Leu Ser Lys Leu
            20                  25
```